US008280643B2

(12) United States Patent
Hook et al.

(10) Patent No.: US 8,280,643 B2
(45) Date of Patent: Oct. 2, 2012

(54) CRYSTAL STRUCTURE OF *STAPHYLOCOCCUS AUREUS* CLUMPING FACTOR A IN COMPLEX WITH FIBRINOGEN DERIVED PEPTIDE AND USES THEREOF

(75) Inventors: Magnus Hook, Houston, TX (US); Ya-Ping Ko, Houston, TX (US); Emanuel Smeds, Houston, TX (US); Vannakambadi K. Ganesh, Pearland, TX (US)

(73) Assignee: The Texas A & M University System, College Station, TX (US)

( * ) Notice: Subject to any disclaimer, the term of this patent is extended or adjusted under 35 U.S.C. 154(b) by 190 days.

(21) Appl. No.: 12/459,327

(22) Filed: Jun. 30, 2009

(65) Prior Publication Data

US 2010/0015138 A1 Jan. 21, 2010

Related U.S. Application Data

(60) Provisional application No. 61/133,537, filed on Jun. 30, 2008.

(51) Int. Cl.
*G06F 19/00* (2011.01)
*G01N 31/00* (2006.01)

(52) U.S. Cl. .......................................................... 702/19

(58) Field of Classification Search ........................ None
See application file for complete search history.

(56) References Cited

U.S. PATENT DOCUMENTS

| | | | | |
|---|---|---|---|---|
| 5,773,577 | A | 6/1998 | Cappello | |
| 6,037,457 | A | 3/2000 | Lord | |
| 6,083,902 | A | 7/2000 | Cederhom-Williams | |
| 6,177,084 | B1 | 1/2001 | Foster et al. | |
| 2002/0159997 | A1 | 10/2002 | Patti et al. | 424/142.1 |
| 2003/0044418 | A1 | 3/2003 | Davis et al. | |
| 2004/0019189 | A1 | 1/2004 | Sallberg | |
| 2006/0239958 | A1 | 10/2006 | Taguchi et al. | |
| 2006/0276621 | A1 | 12/2006 | Sallberg | |

FOREIGN PATENT DOCUMENTS

EP 0126666 A1 4/1984

OTHER PUBLICATIONS

Ponnuraj et al. (Cell (2003) vol. 115, pp. 217-228).*
Deivanayagam et al. (The EMBO Journal (2002) vol. 21, pp. 6660-6672).*
Wann et al. (The Hournal of Biological Chemistry (2000) vol. 275, pp. 13863-13871).*
International Search Report and Written Opinion for PCT/US2009/003872 dated Mar. 16, 2010.
Xiao, Tsan, et al., "Structural Basis for Allostery in Integrins and Binding to Fibrinogen-Nimetic Therapeutics," Nature, vol. 432, Nov. 4, 2004, pp. 59-67.
Xiong, Jian-Ping, et al., "Srystal Structure of the Extracellular Segment of Integrin aVb3 in Complex with an Arg-Gly-Asp Ligand," Science 296, (2002), pp. 151-155.
Zong, Yinong, et al., "A Collagen Hug Model for *Staphylococcus Aureus* CNA Binding to Collagen, " EMBO Journal, vol. 24, No. 24, (2005), pp. 4224-4236.
International Search Report and Written Opinion for PCT/US2010/054882, dated Aug. 23, 2011.
Altschul, Stephen F., et al., "Basic Local Alignment Search Tool," J. Mol. Biol. (1990), 215, pp. 403-410.
Bowden, M.G., et al., "Evidence for the Dock, Lock and Latch Ligand Binding Mechanism of the *Staphylococcal* Microbial Surface Component Recognizing Adhesive Matrix Molecules (MSCRAMM)," J. Biol Chem, vol. 283, No. 1, Jan. 4, 2008, pp. 638-647.
Carson, M.J., "Ribbon Models for Macromolecules," J. Mol. Graph., 5, pp. 103-106, 1987.
Colman, Robert W., et al., "Hemostatis and Thrombosis: Basic Principles and Clinical Practice," (1994) Philadelphia, J.B. Lippincott Company, 51 pages.
Davis, Stacey L., et al., "SdrG, A Fibrinogen-Binding Bacterial Adhesin of the Microbial Surface Components Recognizing Adhesive Matrix Molecules Subfamily from *Staphylococcus epidermidis*, Targets the Thrombin Cleavage Site in the Bβ Chain,", J. Biol. Chem 2001 vol. 276; 27799-27805.
Deivanayagam, et al., "A Novel Variant of the Immunoglobulin Fold in Surface Adhesins of *Staphylococcus aureus*: Crystal Structure of the Fibrogen-Binding MSCRAMM, Clumping Factor A," EMBO Journal, vol. 21, No. 24, pp. 6660-6672 (2002).
Dinges, Martin M., et al., "Exotoxins of *Staphylococcus aureus*," Clinical Microbiology Reviews, vol. 13, No. 1, Jan. 2000, pp. 16-34.
Domanski, et al., Characterization of a Humanized Monoclonal Antibody Recognizing Clumping Factor A Expressed by *Staphylococcus aureus*, Infection and Immunity, Aug. 2005, vol. 73, No. 8, pp. 5229-5232. Emsley, Paul, et al., "Coot: Model-Building Tools for Molecular Graphics," Acta Cryst. (2004), pp. 2126-2132.
Farrell, David H., et al., "Role of Fibrogen α and y Chain Sites in Platelet Aggregation," Proc. Natl. Acad. Sci., vol. 89, Nov. 1992, pp. 10729-10732.
Foster, Timothy J., et al., "Surface Protein Adhesins of *Staphylococcus aureus*," Trends in Mircobiology, vol. 6, No. 12, Dec. 1998, pp. 484-488.
Foster, Timothy J., "Immune Evasion by *Staphylococci*," Nature, vol. 3, Dec. 2005, pp. 948-958.

(Continued)

*Primary Examiner* — Lori A Clow
(74) *Attorney, Agent, or Firm* — Chainey P. Singleton; Edwin S. Flores; Chalker Flores, LLP

(57) ABSTRACT

The present invention provides a method for determining the structure of a microbial surface components recognizing adhesive matrix molecule in complex with fibrinogen, by providing a ClfA complexed with a fibrinogen gamma-peptide; determining a ClfA binding region of the fibrinogen gamma-peptide; determining one or more critical amino acid residues in the ClfA binding region of a native fibrinogen gamma-peptide that is critical for a ClfA:fibrinogen gamma-peptide interaction; determining one or more amino acid residues of the ClfA that binds to the ClfA binding region of the native fibrinogen gamma-peptide; modeling the structure of the ClfA binding region; determining the structure of the ClfA in complex with the :fibrinogen gamma-peptide interaction; and identifying one or more potential agent(s) that inhibit the ClfA:fibrinogen gamma-peptide interaction without affecting binding of other proteins to the fibrinogen gamma-peptide.

8 Claims, 14 Drawing Sheets

OTHER PUBLICATIONS

Ganesh, V.K., et al., "A Structural Model of the *Staphylococcus aureus* ClfA-Fibrinogen Interaction Opens New Aenues for the Design of Anti-Staphylococcal Therapeutics," PLOS Pathogens, Nov. 2008, vol. 4, Issue 11, pp. 1-10.

Hall, Andrea E., et al., "Characterization of a Protective Monoclonal Antibody Recognizing *Staphylococcus aureus* MSCRAMM Protein Clumping Factor A," Infection and Immunity, Dec. 2003, pp. 6864-6870.

Hartford, Orla M., et al., "Identification of Residues in the *Staphylococcus aureus* Fibrinogen-binding MSCRAMM Clumping Factor A (ClfA) that are Important for Ligand Binding," The Journal of Biological Chemistry, vol. 276, No. 4, pp. 2466-2473, (2001).

Hettasch, et al., "The Residues AGDV of Recombinant y Chains of Human Fibrinogen Must Be Carboxy-Terminal to Support Human Platelet Aggregation," Thrombosis and Haemostasis, (1992), pp. 701-706.

Ho, Steffan N., et al., "Site-Directed Mutagenesis by Overlap Extension Using the Polymerase Chain Reaction," Gene, 77, (1989), pp. 51-59.

Horton, Robert M., et al., "Gene Splicing by Overlap Extension: Tailor-Made Genes Using the Polymerase Chain Reaction," BioTechniques, vol. 8, No. 5, (1990), pp. 528-535.

Huang, Xiaoqiu, "A Time-Efficient, Linear-Space Local Similarity Algorithm," Advances in Applied Mathematics 12, pp. 337-357, (1991).

Josefsson, Elisabet, et al., "Protection Against Experimental *Staphylococcus aureus* Arthritis by Vaccinationwith Clumping Factor A, a Novel Virulence Determinant," The Journal of Infectious Diseases, (2001), pp. 1572-1580.

Keane, Fiona M., et al., "Fibrinogen and Elastin Bind to the Same Region within the A Domain of Fibronectin Binding Protein A, an MSCRAMM of *Staphylococcus aureus*," Molecular Microbiology, (2007), 63(3), pp. 711-723.

Kloczewiak, Marek, et al., "Platelet Receptor Recognition Domain on the y Chain of Human Fibrogen and its Synthetic Peptide Analogues," Biochemistry, 28, pp. 2915-2919, (1989).

Kristinsson, K.G., "Adherence of *Staphylococi* to Intravascular Catheters," J. Med. Microbiol., vol. 28, pp. 249-257, (1989).

Laskowski, Roman A., et al., "Main-Chain Lengths and Bond Angles in Protein Structures," J. Mol. Biol. 231, pp. 1049-1067, (1993).

Liu, et al., "ClfA (221-550), A Fibrinogen-Binding Segment of *Staphylooccus aureus* Clumping Factor A, Disrupts Fibrinogen Function," Thromb Haemost, (2005), 94(2):286-294.

Lowy, Franklin D., "*Staphylococcus aureus* Infections," The New England Journal of Medicine, Aug. 20, 1998, pp. 520-532.

Maltezou, Helen C., et al., "Community-Acquired Methicillin-Resistant *Staphylococcus aureus* Infections," International Journal of Antimicrobial Agents 27 (2006), pp. 87-96.

Marraffini, Luciano A., et al., "Sortases and the Art of Anchoring Proteins to the Envelopes of Gram-Positive Bacteria," Microbiology and Molecular Biology Reviews, vol. 70, No. 1, Mar. 2006, pp. 192-221.

Mazmanian, Sarkis K., et al., "Sortase-Catalysed Anchoring of Surface Proteins to the Cell Wall of *Staphylococcus aureus*," Molecular Microbiology, 40 (5), (2001), pp. 1049-1057.

McCoy, Airlie J., et al., "Likelihood-Enhanced Fast Translation Functions," Acta Cryst. (2005), pp. 458-464.

McDevitt, D., et al., "Molecular Characterization of the Clumping Factor (Fibrinogen Receptor) of *Staphylococcus aureus*," Molecular Microbiology, (1994), 11(2), pp. 237-248.

McDevitt, D., et al., "Identification of the Ligand-Binding Domain of the Surface-Located Fibrinogen Receptor (Clumping Factor) of *Staphylococcus aureus*," Molecular Microbiology, (1995), 16(5), pp. 895-907.

McDevitt, D., et al., "Characterization of the Interaction Between the *Staphylococcus aureus* Clumping Factor (ClfA) and Fibrinogen," Eur. J. Biochem, 247, (1997), pp. 416-424.

Murshudov, Garib N., et al., "Refinement of Macromolecular Structures by the Maximum-Likelihood Method," Acta Cryst. D53, (1997), pp. 240-255.

Ni Eldhin, Deirdre, et al., "Clumping Factor B (ClfB), a New Surface-Located Fibrinogen-Binding Adhesin of *Staphylococcus aureus*," Molecular Microbiology, 30(2), (1998), pp. 245-257.

O'Brien, Louise, et al., "Multiple Mechanisms for the Activation of Human Platelet Aggregation by *Staphylococcus aureus*: Roles for the lumping Factors ClfA and ClfB, the SAerine-aspartate Repeat Protein SdrE and Protein A," Molecular Microbiology, 44(4), (2002), pp. 1033-1044.

O'Connell, David P., et al., "The Fibrinogen-Binding MSCRAMM (Clumping Factor) of *Staphylococcus aureus* Has a Ca2+-Dependent Inhibitory Site," The Journal of Biological Chemistry, vol. 273, No. 12, Mar. 20, 1998; pp. 6821-6829.

O'Riordan, Katherine, et al., "*Staphylococcus aureus* Capsular Polysaccharides," Clinical Microbiology Reviews, vol. 17, No. 1, Jan. 2004, pp. 218-234.

Patti, Joseph M., "A Humanized Monoclonal Antibody Targeting *Staphylococcus aureus*," Vaccine 22S, (2004), pp. S39-S43.

Peacock, Sharon J., et al., "Virulent Combinations of Adhesin and Toxin Genes in Natural Poplulations of *Staphylococcus aureus*," Infection and Immunity, Sep. 2002, pp. 4987-4996.

Perrakis, Anastassis, et al., ARP/wARP and Molecular Replacement, Acta Cryst. (2001), 57, pp. 1445-1450.

Pflugrath, J.W., "The Finer Things in X-Ray Diffraction Data Collection," Acta Cryst. (1999), D55, pp. 1718-1725.

Ponnuraj, Karthe, et al., "A "Dock, Lock and Latch" Structural Model for a *Staphylococcal* Adhesin Binding to Fibrinogen," Cell, vol. 115, Oct. 17, 2003, pp. 217-228.

Que, Yok-Ai, et al., "Reassessing the Role of *Staphylococcus aureus* Clumping Factor and Fibronectin-Binding Protein by Expression in *Lactococcus lactis*," Infection and Immunity, Oct. 2001, pp. 6296-6302.

Rivera, Jose, et al., "Fibrinogen-Binding Proteins of Gram-Positive Bacteria," THromb Haemost, (2007), 98:503-511.

Sambrook, Joe, et al., "Chaperones, Paperones," Nature, vol. 342, Nov. 16, 1989, pp. 224-225.

Siboo, Ian R., et al., "Clumping Factor A Mediates Binding of *Staphylococcus aureus* to Human Platelets," Infection and Immunity, vol. 69, No. 5, May 2001, pp. 3120-3127.

Sullam, Paul M., et al., "Diminished Platelet Binding in Vitro by *Staphylococcus aureus* is Associated with Reduced Virulence in a Rabbit Model of Infective Endocarditis," Infection and Immunity, vol. 64, No. 12, Dec. 1996, pp. 4915-4921.

Wann, Elisabeth R., et al., "The Fibronectin-Binding MSCRAMM FnbpA of *Staphylococcus aureus* is a Bifunctional Protein that Also Binds to Fibrinogen," The Journal of Biological Chemistry, vol. 275, No. 18, May 5, 2000, pp. 13863-13871.

Weber, J. Todd, "Community-Associated Methicillin-Resistant *Staphylococcus aureus*," Clinical Infectious Diseases, (2005), pp. S269-S272.

* cited by examiner

| | | | |
|---|---|---|---|
| GEGQQHHLGGAKQAGDV | Fg WT $\gamma^{1-17}$ (395-411) | | SEQ ID NO: 6 |
| AEGQQHHLGGAKQAGDV | P1 | G1A | SEQ ID NO: 14 |
| GAGQQHHLGGAKQAGDV | P2 | E2A | SEQ ID NO: 15 |
| GEAQQHHLGGAKQAGDV | P3 | G3A | SEQ ID NO: 16 |
| GEGAQHHLGGAKQAGDV | P4 | Q4A | SEQ ID NO; 17 |
| GEGQAHHLGGAKQAGDV | P5 | Q5A | SEQ ID NO: 18 |
| GEGQQAHLGGAKQAGDV | P6 | H6A | SEQ ID NO: 19 |
| GEGQQHALGGAKQAGDV | P7 | H7A | SEQ ID NO: 20 |
| GEGQQHHAGGAKQAGDV | P8 | L8A | SEQ ID NO: 21 |
| GEGQQHHLAGAKQAGDV | P9 | G9A | SEQ ID NO: 22 |
| GEGQQHHLGAAKQAGDV | P10 | G10A | SEQ ID NO: 23 |
| GEGQQHHLGGSKQAGDV | P11 | A11S | SEQ ID NO: 24 |
| GEGQQHHLGGAAQAGDV | P12 | K12A | SEQ ID NO: 25 |
| GEGQQHHLGGAKAAGDV | P13 | Q13A | SEQ ID NO: 26 |
| GEGQQHHLGGAKQSGDV | P14 | A14S | SEQ ID NO: 26 |
| GEGQQHHLGGAKQAADV | P15 | G15A | SEQ ID NO: 27 |
| GEGQQHHLGGAKQAGAV | P16 | D16A | SEQ ID NO: 28 |
| GEGQQHHLGGAKQAGDA | P17 | V17A | SEQ ID NO: 29 |
| | | | SEQ ID NO: 30 |

Fig. 1A

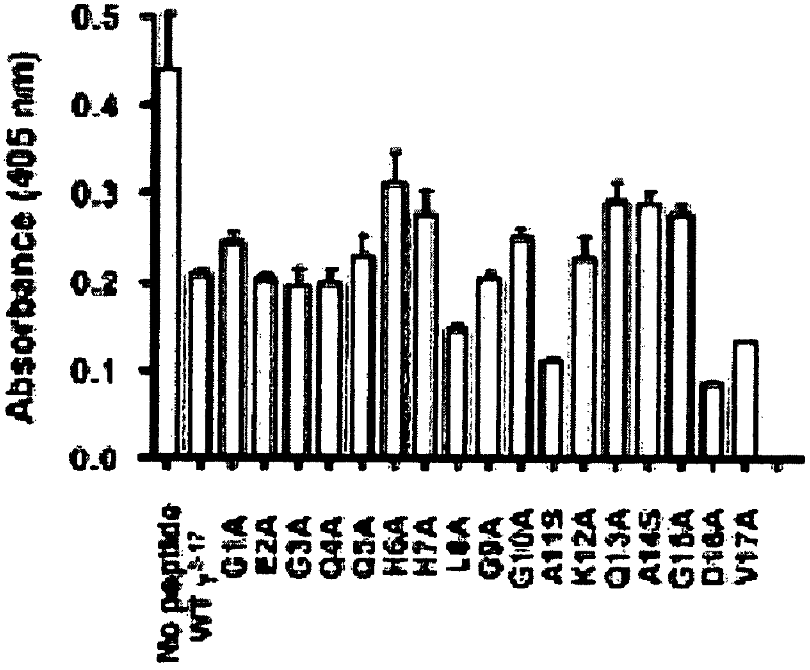

Fig. 1B

| Peptide | Sequence | |
|---|---|---|
| Fg γ1-17 | GEGQQHHLGGAKQAG**A**V | SEQ ID NO: 28 |
| Fg γ3-17 | GQQHHLGGAKQAG**A**V | SEQ ID NO: 7 |
| Fg γ5-17 | QHHLGGAKQAG**A**V | SEQ ID NO: 8 |
| Fg γ7-17 | HLGGAKQAG**A**V | SEQ ID NO: 8 |
| Fg γ9-17 | GGAKQAG**A**V | SEQ ID NO: 10 |
| Fg γ1-15 | GEGQQHHLGGAKQAG | SEQ ID NO: 11 |
| Fg γ1-13 | GEGQQHHLGGAKQ | SEQ ID NO: 12 |

CRYSTAL STRUCTURE OF *STAPHYLOCOCCUS AUREUS* CLUMPING FACTOR A IN COMPLEX WITH FIBRINOGEN DERIVED PEPTIDE AND USES THEREOF

CROSS-REFERENCE TO RELATED APPLICATIONS

This non-provisional application claims benefit of priority under 35 U.S.C. §119(e) of provisional U.S. Ser. No. 61/133,537, filed Jun. 30, 2008, the entirety of which is hereby incorporated by reference.

FEDERAL FUNDING LEGEND

This invention was produced using funds obtained through a National Institutes of Health grant (AI20624). Consequently, the Federal government has certain rights in this invention.

BACKGROUND OF THE INVENTION

1. Field of the Invention

The present invention relates generally to the fields of protein chemistry, immunology, therapeutic pharmaceuticals, and vaccine development. More specifically, the present invention discloses crystal structure of *Staphylococcus aureus* clumping factor A (ClfA) in complex with fibrinogen (Fg) derived peptide and its use in the design of ClfA targeted vaccines and therapeutic agents (including monoclonal antibodies).

2. Description of the Related Art

*Staphylococcus aureus* is a Gram-positive commensal organism that permanently colonizes 20% of healthy adults and transiently colonizes up to 50% of the population (1). For many years, *S. aureus* has been a major nosocomial pathogen causing a range of diseases from superficial skin infections to life-threatening conditions, including septicemia, endocarditis and pneumonia (1-2). Within the last decade an increasing number of invasive infections caused by community-acquired *S. aureus* have been recorded in otherwise healthy children and young adults (3-4). The continued emergence of antibiotic resistance among clinical strains has made the treatment of staphylococcal infections challenging, underscoring the need for new prevention and treatment strategies (1).

A detailed characterization of the molecular pathogenesis of *S. aureus* infections may expose new targets for the development of novel vaccines and therapeutics. Several staphylococcal virulence factors have been identified including capsule, surface adhesins, proteases, and toxins (5-8). One of these virulence factors is the MSCRAMM clumping factor A (ClfA). ClfA is the major staphylococcal fibrinogen (Fg) binding protein and is responsible for *S. aureus* clumping in blood plasma (9-10). Essentially all *S. aureus* clinical strains carry the clfA gene (11); ClfA is a virulence factor in a mouse model of septic arthritis (12) and in rabbit and rat models of infective endocarditis (13-15).

ClfA generates strong immune responses and has shown potential as a vaccine component in active and passive immunization studies. In one study, mice vaccinated with a recombinant ClfA segment containing the Fg-binding domain and subsequently infected with *S. aureus* showed significantly lower levels of arthritis (12). In another study, mice passively immunized with polyclonal or monoclonal antibodies against the ClfA Fg-binding domain were protected in a model of septic death (16). The humanized monoclonal antibody, Aurexis®, has a high affinity for ClfA and inhibits ClfA binding to Fg (17). Aurexis is currently in clinical trials in combination with antibiotic therapy for the treatment of *S. aureus* bacteremia (18).

ClfA belongs to a class of cell wall-localized proteins that are covalently anchored to the peptidoglycan (6, 19-20). Starting from the N-terminus, ClfA contains a signal sequence followed by the ligand-binding A region composed of three domains (N1, N2, and N3), the serine-aspartate repeat domain (R region), and C-terminal features required for cell wall anchoring such as the LPXTG motif, a transmembrane segment and a short cytoplasmic domain (21-23). A crystal structure of a Fg-binding ClfA segment (residues 221-559) which includes two of the domains (N2N3) demonstrates that each domain adopts an IgG-like fold (24). This domain architecture was also determined from the crystal structure of the ligand binding segment of the *Staphylococcus epidermidis* SdrG, an MSCRAMM that binds to the N-terminal region of the Fg β-chain (25).

Molecular modeling and sequence analysis indicated that the staphylococcal Fg binding MSCRAMMs ClfB and FnbpA could also have a structural organization similar to that of SdrG and ClfA, setting the stage for a common mechanism of ligand binding. For SdrG, a dynamic mechanism of Fg binding termed "Dock, Lock and Latch" (DLL) has been proposed based on a comparison of the crystal structures of SdrG N2N3 as an apo-protein and in complex with a synthetic peptide mimicking the targeted site in Fg (25). In the SdrG DLL model, the apo-form of the protein adopts an open conformation that allows the Fg ligand access to a binding trench between the N2 and N3 domains. As the ligand peptide docks into the trench, a flexible C-terminal extension of the N3 domain is redirected to cover the ligand peptide and "lock" it in place. Subsequently the C-terminal part of this extension interacts with the N2 domain and forms a β-strand complementing a β-sheet in the N2 domain. This inserted β-strand serves as a latch to form a stable MSCRAMM ligand complex.

ClfA binds to the C-terminus of the Fg γ-chain (9, 23) and a synthetic 17 amino acid peptide corresponding to this region was shown to bind to ClfA. Interestingly, the A-region of another staphylocccal MSCRAMM FnbpA protein and human platelet $\alpha_{IIb}\beta_3$ integrin also binds to the same region in Fg (23, 26-28). A recombinant form of ClfA has been shown to inhibit platelet aggregation and the binding of platelets to immobilized Fg (9). Although the individual N2 and N3 subdomains in SdrG and ClfA are structurally similar, the overall orientation of one with respect to the other is different.

Thus, prior art is deficient in structural characterization of how ClfA binds Fg and its use in the design of vaccines and therapeutic compounds for the prevention and treatment of staphylococcal infections. The current invention fulfils this long standing need in the art.

SUMMARY OF THE INVENTION

The present invention discloses crystal structure of *Staphylococcus aureus* clumping factor A (ClfA) in complex with fibrinogen (Fg) derived peptide. Further, the present invention also discloses the use of this structure and any structural information in the design of ClfA targeted vaccines and therapeutic agents (including monoclonal antibodies).

The present invention is directed to a therapeutic agent that binds Microbial Surface Components Recognizing Adhesive Matrix Molecules (MSCRAMM) with higher binding affinity than native fibrinogen (Fg). A representative agent comprises an amino acid sequence that differs from amino acid sequence of a native fibrinogen in at least one amino acid residue.

The present invention also is directed to an anti-MSCRAMM:fibrinogen antibody effective to inhibit MSCRAMM:fibrinogen interaction but does not affect binding of other proteins to fibrinogen.

The present invention is directed further to a method for determining model structure of MSCRAMM in complex with fibrinogen. Such a method comprises determining amino acid residue in the MSCRAMM binding region of native fibrinogen that is critical for the MSCRAMM:fibrinogen interaction; determining amino acid residue of the MSCRAMM that binds to said MSCRAMM binding region of native fibrinogen; and performing computational modeling of the MSCRAMM sequence that binds to the MSCRAMM binding region of native fibrinogen, thereby determining the structure of the MSCRAMM in complex with the fibrinogen.

The present invention is directed further still to a crystal structure of a *Staphylococcus* clumping factor A (ClfA) protein:fibrinogen derived peptide complex that diffracts x-rays for determining atomic coordinates of the complex with a resolution of about 1.95 angstroms.

The present invention is directed further still to an engineered stabilized (closed form) of ClfA that binds fibrinogen with higher affinity as an efficient vaccine candidate. The present invention is directed to a related immunogenic composition comprising the ClfA protein described herein and an immunologically acceptable adjuvant or diluent. The present invention also is directed to a related a method of vaccinating an individual against a *Staphylococcus* infection comprising administering an immunologically effective amount of the immunogenic composition to the individual.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIGS. 1A-1D demonstrate that $ClfA_{229-545}$ binds to Fg g chain peptides. FIG. 1A shows a panel of Fg γ-chain peptides. The wild-type peptide corresponds to the 17 C-terminal residues of the Fg g-chain (395-411); the mutated peptides have individual amino acids replaced with Ala (or Ser). FIG. 1B shows that Fg γ peptides inhibit ClfA binding to immobilized GST-Fg γ in solid phase assays. Wells were coated with 1 mg GST-Fg γ peptide. $ClfA_{229-545}$ (100 nM) was pre-incubated with wild-type Fg γ peptide (WT $g^{1-17}$) or the P1 (G1A) to P17 (V17A) mutant peptide (50 mM) for 1 hr. FIG. 1C shows the binding of ClfA to immobilized GST-Fg γ and GST-Fg γ P16 using a solid-phase assay. Increasing concentrations of $rClfA_{229-545}$ were incubated in microtiter wells containing 1 mg GST (circles), GST-Fg γ (triangles) or GST-Fg g P16 (squares). Bound ClfA was detected with anti-His monoclonal antibodies as described. FIG. 1D shows the binding of $ClfA_{229-545}$ to Fg γ and Fg γ P16 peptides in solution using ITC.

FIG. 2A shows a panel of Fg γ P16 peptides with N- and C-terminal truncations. FIG. 2B shows N-terminal deletions of Fg γ P16 peptide bind $ClfA_{229-545}$ with decreasing affinities. N- and C-terminal truncated Fg γ P16 peptides were tested for their ability to bind $ClfA_{229-545}$ in solution using ITC. FIG. 2C shows a stable closed conformation $ClfA_{229-545}$ was engineered by introducing a disulfide bridge. The left panel shows a ligand blot of $rClfA_{D327C/K5_{41C}}$. Recombinant proteins were run in an SDS-PAGE in the presence or absence of 5 mM DTT and stained with Coomassie Blue (left panel) or transferred to a PDVF membrane (middle panel). Transferred proteins were probed with Fg (10 mg/ml) and detected with anti-Fg and AP-conjugated secondary antibodies. (Right panel) The purified closed form of $ClfA_{327C/541C}$ used for crystallization and $ClfA_{229-545}$ were run in an SDS-PAGE and stained with Coomassie Blue (right panel). FIG. 2D shows the closed conformation of $ClfA_{D327C/K541C}$ binds immobilized Fg and GST-Fg γ P16. $ClfA_{229-545}$ or $ClfA_{D327C/K541C}$ was incubated with wells coated with either Fg or GST-Fg γ P16 and detected with anti-His monoclonal antibodies as described below.

FIG. 3A is the ribbon representation of ClfA-peptide (Fg γ-chain analog) complex. The peptide is shown as ball and stick model. 2Fo-Fc map around the peptide contoured at 1σ is shown in the close-up view. FIG. 3B is a stereo view of the superposition of the two complexes (A:C and B:D) in the asymmetric unit. FIG. 3C is a schematic representation of ClfA-Fg γ-peptide main-chain parallel β-complementation interaction. The anti-parallel β-complementation observed in $SdrG_{273-597}$-Fg β-peptide complex is also shown for comparison. The residue numbers of both the Fg γ-chain sequence and the peptide numbering (1-17), in parenthesis, are shown. FIG. 3D is a stereo-view showing the side-chain interactions of the ClfA-Fg γ-peptide complex. Carbon atoms of the peptide are shown in grey; oxygen, red; nitrogen, blue. Side chain atoms of ClfA are shown as pink stick objects. Hydrogen bonds are shown as dotted lines.

FIG. 4A shows the superposition of apo-$ClfA_{221-559}$, $ClfA_{D327C/K541C}$-peptide complex. The N3 domains of the two structures are superposed showing significant deviation in the inter-domain orientations. Apo-ClfA is shown as a cyan ribbon object and ClfA-peptide complex is shown in green. In FIG. 4B only N3 domain of apo-ClfA (cyan) is shown for clarity. The folded-back residues of the C-terminal residues of the apo-ClfA are shown in red. The Fg γ-chain peptide is shown as blue ribbon. FIG. 4C shows the superposition of ClfA-peptide and SdrG-peptide complexes. The peptide molecules corresponding to ClfA and SdrG complexes are shown as red and blue ribbon objects respectively. ClfA is colored by secondary structure and SdrG is shown as thin yellow uniform coil.

FIG. 5A shows that the closed conformation $rClfA_{327C/541C}$ binds immobilized Fg from different animal species with different apparent affinities in a solid-phase assay. FIG. 5B shows that the $ClfA_{D327C/K541C}$ binds human Fg γ P16 peptide with a higher affinity than bovine Fg γ peptide using ITC. FIG. 5C shows that the sequence comparison of human and bovine Fg γ-chain C-terminal residues (top). CPK representation of the binding pocket formed between the N2 and N3 domains bound to human versus bovine Fg γ peptide. ClfA is shown as grey CPK object and peptide atoms are shown in black (bottom).

FIG. 7A shows that Fg γ peptides inhibit $FnbpA_{194-511}$ binding to immobilized GST-Fg γ. Wells were coated with 1 mg GST-Fg γ peptide. $FnbpA_{194-511}$ (400 nM) was pre-incubated with wild-type Fg γ peptide (WT $\gamma^{1-17}$) or the P1 (G1A) to P17 (V17A) mutant peptide (50 mM) for 1 hr. FIG. 7B is the ribbon representation of $FnbpA_{194-511}$: Fg-γ-chain peptide binding model. N2 and N3 domains in FnbpA are shown as ribbons and peptide is shown as stick object.

DETAILED DESCRIPTION OF THE INVENTION

I. Definitions

Figure 1C:
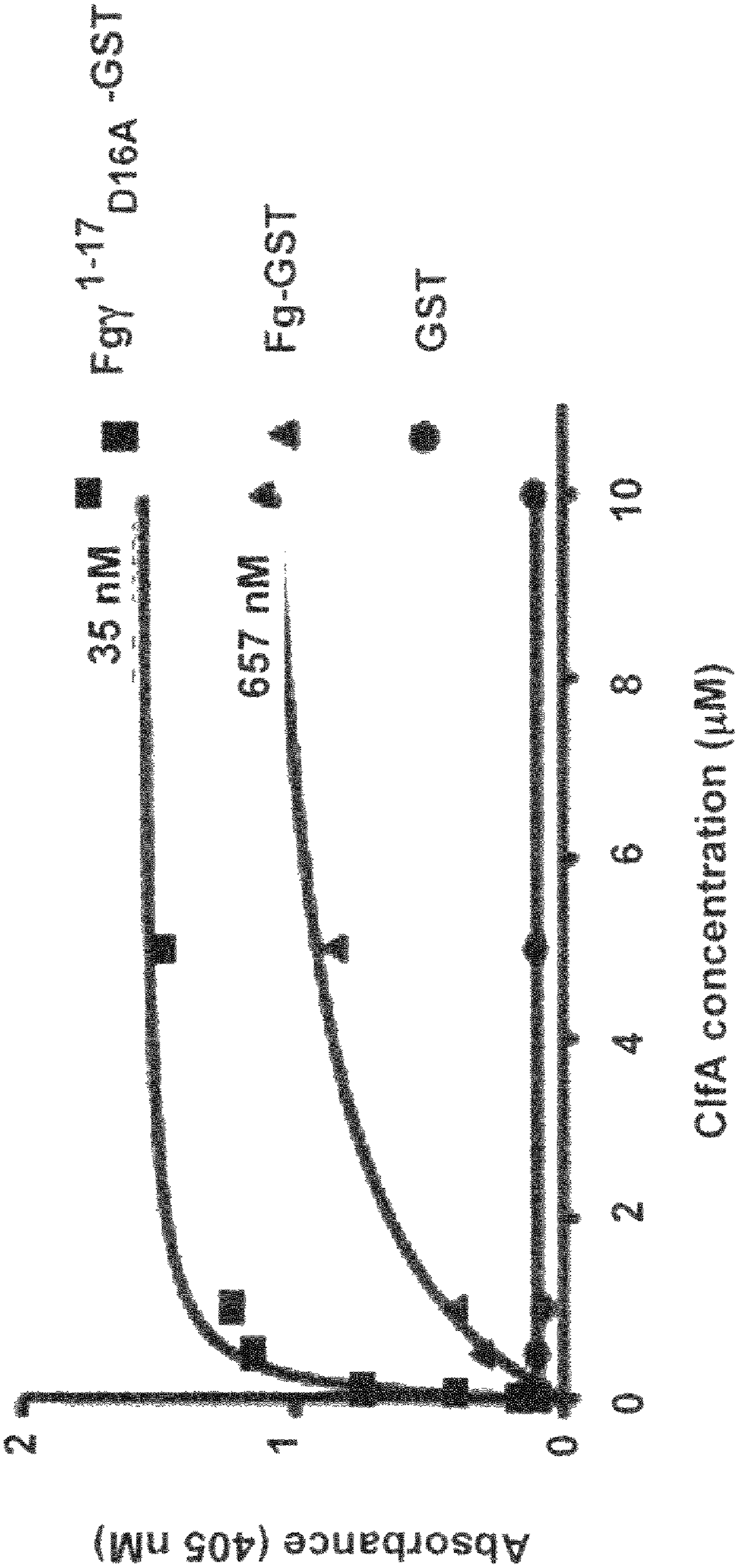

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "immunologically effective amount" refers to an amount that results in an improvement or remediation of the symptoms of the disease or condition due to induction of an immune response. Those of skill in the art understand that the effective amount may improve the patient's or subject's condition, but may not be a complete cure of the disease and/or condition.

As used herein, "active immunization" is defined as the administration of a vaccine to stimulate the host immune system to develop immunity against a specific pathogen or toxin.

As used herein, "passive immunization" is defined as the administration of antibodies to a host to provide immunity against a specific pathogen or toxin.

As used herein, "CpG oligonucleotides" are defined by the presence of an unmethylated CG dinucleotide in a CpG motif.

As used herein, "adjuvant" is defined as a substance which when included in a vaccine formulation non-specifically enhances the immune response to an antigen.

II. Present Invention

In one embodiment of the present invention there is provided a therapeutic agent that binds Microbial Surface Components Recognizing Adhesive Matrix Molecules (MSCRAMM) with higher binding affinity than native fibrinogen (Fg), the agent comprising amino acid sequence that differs from amino acid sequence of a native Fibrinogen in at least one amino acid residue. Examples of such an agent may include but is not limited to a peptide, a fusion protein, a small molecule inhibitor or a small molecule drug. Examples of the peptide may include but is not limited to a P16 peptide (Asp16→Ala), a P12 peptide (Lys12→Ala) or combination thereof. Further, examples of MSCRAMM may include but is not limited to a clumping factor A (ClfA), FnbpA, FnbpB or Fbl and the MSCRAMM may include but is not limited to those present on the surface of *Staphylococcus aureus, Staphylococcus lugdunensis*, or *Staphylococcus epidermis.*

In another embodiment of the present invention there is provided a method for inhibiting Microbial Surface Components Recognizing Adhesive Matrix Molecule (MSCRAMM):Fibrinogen (Fg) interaction, comprising: contacting an MSCRAMM with the above-described therapeutic agent, thereby inhibiting the MSCRAMM:Fibrinogen interaction. The therapeutic agent may not affect $\alpha_{IIb}\beta_3$ intergrin interaction.

In yet another embodiment of the present invention there is provided a pharmaceutical composition, comprising: the above-described therapeutic agent and a pharmaceutically acceptable carrier.

In yet another embodiment of the present invention there is provided a method of treating and/or preventing bacterial infection caused or due at least in part to a MSCRAMM: fibrinogen interaction in an individual, comprising: administering pharmacologically effective amounts of the pharmaceutical composition described supra such that administration of the composition inhibits binding of MSCRAMM to native fibrinogen and does not affect $\alpha_{IIb}\beta_3$ intergrin interaction. Examples of the bacteria may include but is not limited to *Staphylococcus aureus, Staphylococcus lugdunensis*, or *Staphylococcus epidermis*. Further, the routes of administration of the pharmaceutical composition may include but is not limited to subcutaneous, intravenous, intramuscular, intra nasal, vaginal, or oral routes. One of ordinary skill in the art is readily able to determine a suitable dosage. Additionally, the individual who may benefit from such a method may include but is not limited to one who is a healthy individual, an individual diagnosed with the bacterial infection, at risk of developing bacterial infection or suspected of suffering from the bacterial infection.

In yet another embodiment of the present invention there is provided an anti-MSCRAMM:fibrinogen antibody effective to inhibit an MSCRAMM:fibrinogen interaction but not affecting binding of other proteins to fibrinogen. Such an antibody may be generated using peptides comprising MSCRAMM binding region on fibrinogen, the peptide differing from the native Fibrinogen in at least one amino acid residue. Examples of the peptide may include but is not limited to a P16 peptide (Asp16→Ala), a P12 peptide (Lys12→Ala) or combination thereof. Alternatively, the antibody may be generated using peptides derived from fibrinogen binding region of MSCRAMM, the peptide differing from the native MSCRAMM in at least one amino acid residue. Further, the antibody may be a monoclonal antibody, a polyclonal antibody or a chimeric antibody. Furthermore, the MSCRAMM may be present on *Staphylococcus aureus, Staphylococcus lugdunensis*, or *Staphylococcus epidermis.*

In yet another embodiment of the present invention there is provided a method of treating a bacterial infection in an individual, comprising: administering immunologically effective amounts of the above-described anti-MSCRAMM: fibrinogen antibody to the individual, thereby treating the bacterial infection in the individual. Such an antibody may inhibits interaction between MSCRAMM and Fibrinogen may not affect the $\alpha_{IIb}\beta_3$ intergrin interaction. Examples of the individual who may benefit from this method may include but is not limited to one who is diagnosed with the infection, is at risk of developing the infection or is suspected of suffering from the infection. One of ordinary skill in the art is readily able to determine a suitable dosage. Further, examples of the routes of administration of the antibody may include subcutaneous, intramuscular, intravenous, intranasal, vaginal, oral, or other mucosal routes.

In yet another embodiment of the present invention there is provided a method for determining structure of MSCRAMM in complex with fibrinogen, comprising: determining amino acid residue in the MSCRAMM binding region of native fibrinogen that is critical for the MSCRAMM:fibrinogen interaction; determining amino acid residue of the MSCRAMM that binds to the MSCRAMM binding region of native fibrinogen; and performing computational modeling of the MSCRAMM sequence that binds to the MSCRAMM binding region of native fibrinogen, thereby determining the structure of the MSCRAMM in complex with the fibrinogen. This method may further comprise identifying potential agents that inhibit MSCRAMM:fibrinogen interaction without affecting binding of other proteins to fibrinogen. Such a potential agent may include one that comprises amino acid sequence of MSCRAMM binding region on fibrinogen, the amino acid sequence differing from the fibrinogen in at least one amino acid residue or an amino acid sequence of fibrinogen binding region of MSCRAMM, the amino acid sequence differing from the MSCRAMM in at least one amino acid residue.

Additionally, the amino acid residue in the MSCRAMM binding region of native fibrinogen may be determined by: synthesizing control peptides that comprise the native fibrinogen sequence that binds MSCRAMM; synthesizing substituted peptides that differ from the control peptide in one or more amino acid residues; and comparing binding of MSCRAMM to native fibrinogen in presence of control peptide or in presence of substituted peptide, where less potent inhibition of MSCRAMM binding to native fibrinogen in presence of substituted peptide compared to control peptide indicates that the amino acid residue(s) that were substituted are less important for the MSCRAMM:fibrinogen interaction, where extensive inhibition of MSCRAMM binding to native fibrinogen in presence of substituted peptide compared to control peptide indicates that the amino acid residue(s) that were substituted are critical for the MSCRAMM:fibrinogen interaction.

Further, the amino acid residue in the MSCRAMM may be determined by comparing the stability of a native MSCRAMM:fibrinogen complex with the stability of a mutated MSCRAMM:fibrinogen complex, where said fibrinogen in the complex comprises peptide derived from MSCRAMM binding region of native fibrinogen. Examples of the MSCRAMM may include but is not limited to a clumping factor A (ClfA), FnbpA, FnbpB or Fbl. Further, the MSCRAMM may include but is not limited to one that is present on the surface of *Staphylococcus aureus, Staphylococcus lugdunensis*, or *Staphylococcus epidermis*.

In yet another embodiment of the present invention there is provided a crystal structure of a *Staphylococcus* clumping factor A protein (ClfA):fibrinogen derived peptide complex that diffracts x-rays for determining atomic coordinates of the complex with a resolution of about 1.95 angstroms. The *Staphylococcus* may be those species described supra. In the crystal structure the fibrinogen derived peptide may be a P16 peptide (Asp16→Ala) or a P12 peptide (Lys12→Ala) having an N-terminal truncation-2Nt, -4Nt or -6Nt. Particularly, the crystal structure may be a ClfA/P16-4Nt complex.

In yet another embodiment of the present invention there is provided an isolated and purified engineered *Staphylococcus* clumping factor A protein (ClfA) with a stabilized, closed conformation. For example, the ClfA protein may be $ClfA_{D327C/K541C}$ protein.

In a related embodiment there is provided an immunogenic composition comprising the ClfA protein described supra and an immunologically acceptable adjuvant or diluent. The immunogenic composition may comprise a vaccine.

In another related embodiment there is provided a method of vaccinating an individual against a *Staphylococcus* infection comprising administering an immunologically effective amount of the immunogenic composition described supra to the individual.

The general purpose of the present invention is to provide a detailed structural characterization of how ClfA binds Fg and subsequently use this structural information in the design of vaccines and therapeutic compounds for the prevention and treatment of staphyloccocal infections. Several of the peptides have been shown to have enhanced binding to Fg but show decreased binding to host proteins that target the same region of Fg. The two extensively studied linear peptide binding MSCRAMMs SdrG and ClfA use very similar pockets between the N2 and N3 domains for ligand binding but show significant differences in mechanism of binding. Based on the results presented here, it is postulated that the mechanism of interaction between ClfA and Fg is a variation of the "Dock, Lock and Latch (DLL)" model of SdrG binding to Fg. In the DLL model of binding, the apo-form of the SdrG is in an open conformation to allow the ligand access to the binding cleft. A closed conformation of SdrG is unable to bind Fg. In the ClfA model, it is believed that the peptide may thread into the cavity formed in a stabilized closed configuration and therefore the ClfA-Fg binding mechanism could be called "Latch and Dock".

In the case of CNA, a collagen binding MSCRAMM from *S. aureus*, the collagen molecule binds to CNA through a "collagen hug" model (29) which represents yet another variant of the DLL binding mechanism. All three MSCRAMM-ligand structures determined so far, SdrG, CNA and the ClfA have different ligand binding characteristics and mechanisms, although the overall structures of the ligand binding regions of these MSCRAMMs are very similar. These observations suggest that an ancestral MSCRAMM has evolved to accommodate different ligands without greatly altering the overall organization of the proteins.

Although there are many antibiotics available in the market to treat *S. aureus* infections, the strategy discussed herein is a novel approach targeting ClfA on *S. aureus*. The primary disadvantage of using a small segment (peptide) of the interacting protein molecule is non-specificity and undesirable binding and adverse effects. The process of modified peptide by variations in amino acid will be effective and easier to achieve the much desired specificity. These peptides can be significantly efficient over any small molecule or any other antibiotic treatment. Based on the structure disclosed herein, two peptides, P16 (Asp16→Ala) peptide and P12 (Lys12→Ala) peptide are synthesized and can be used as inhibitors of ClfA. To further enhance the specificity towards ClfA and decrease undesirable activation of platelets, a combination of two variants such as double mutant analog (P12+P16) will be synthesized and tested. The present invention contemplates attempting further variations in the sequence to achieve additional affinity towards ClfA. These peptides are assessed in a mouse model of *S. aureus* induced septic death.

Alternate formulations may include the design of small molecule inhibitors that specifically bind to ClfA and/or tailoring/modify existing small molecule drugs. Several small molecule drugs are available that mimic the same region of Fg that bind to integrin. The features/amino acid differences that contribute to the specificity of the peptide can be incorporated in the existing anti-platelet drug molecules to achieve the specificity for ClfA.

Overall, the present invention provides the Fg/ClfA complex structure that can be (1) used to develop therapeutics that specifically will inhibit ClfA:Fg interaction but will not affect $\alpha_{IIb}\beta_3$ integrin interactions; (2) to design ClfA constructs that will be optimal vaccine candidates and can be used for the generation and screening of therapeutic monoclonal antibodies; and (3) to model other MSCRAMM Fg interactions with similar substrate specificities such as FnbpA, FnbpB and FbI.

Treatment methods involve treating and/preventing an infection in an individual with a pharmacologically effective or an immunologically effective amount of a pharmaceutical composition containing therapeutic agents described herein. Such therapeutic agent may comprise a peptide, fusion peptide, small molecule inhibitor, small molecule drug or an antibody. A pharmacologically effective amount is described, generally, as that amount sufficient to detectably and repeatedly inhibit MSCRAMM:fibrinogen interaction so as to prevent, ameliorate, reduce, minimize or limit the extent of a disease or its symptoms. An immunologically effective amount is described, generally, as that amount sufficient to detectably and repeatedly induce an immune response so as to prevent, ameliorate, reduce, minimize or limit the extent of a disease or its symptoms. More specifically, it is envisioned that the treatment with the pharmaceutical composition or an immunogenic composition enhances antibody response, reduces the level of inflammatory cytokines and the levels of endotoxins and decreases the bacterial load in the individual to prevent the infection caused by the bacteria.

The pharmacologically or immunologically effective amount of the composition or antibody, respectively to be used are those amounts effective to produce beneficial results, particularly with respect to preventing the infection caused by the bacteria, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

The pharmaceutical composition disclosed herein and the antibody generated thereof may be administered either alone or in combination with another drug, a compound, or an antibiotic. Such a drug, compound or antibiotic may be administered concurrently or sequentially with the immunogenic composition or antibody disclosed herein. The effect of co-administration with the pharmaceutical composition or antibody is to lower the dosage of the drug, the compound or the antibiotic normally required that is known to have at least a minimal pharmacological or therapeutic effect against the disease that is being treated. Concomitantly, toxicity of the drug, the compound or the antibiotic to normal cells, tissues and organs is reduced without reducing, ameliorating, eliminating or otherwise interfering with any cytotoxic, cytostatic, apoptotic or other killing or inhibitory therapeutic effect of the drug, compound or antibiotic.

The composition described herein and the drug, compound, or antibiotic may be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The pharmaceutical composition or antibody described herein and the drug, compound or antibiotic may be administered independently one or more times to achieve, maintain or improve upon a therapeutic effect. It is well within the skill of an artisan to determine dosage or whether a suitable dosage of either or both of the immunogenic composition or antibody and the drug, compound or antibiotic comprises a single administered dose or multiple administered doses.

As is well known in the art, a specific dose level of such a pharmaceutical composition or antibody for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

One of skill in the art realizes that the pharmacologically effective amount of the immunogenic composition or the antibody can be the amount that is required to achieve the desired result: enhance antibody response, reduce the level of inflammatory cytokines and levels of endotoxins, decrease the bacterial load, etc.

Administration of the pharmaceutical composition of the present invention and the antibody to a patient or subject will follow general protocols for the administration of therapies used in treatment of bacterial infections taking into account the toxicity, if any, of the components in the immunogenic composition, the antibody and/or, in embodiments of combination therapy, the toxicity of the antibiotic. It is expected that the treatment cycles would be repeated as necessary. It also is contemplated that various standard therapies, as well as surgical intervention, may be applied in combination with the described therapy.

As is known to one of skill in the art the pharmaceutical composition described herein may be administered along with any of the known pharmacologically acceptable carriers. Additionally the pharmaceutical composition can be administered via any of the known routes of administration such as subcutaneous, intranasal or mucosal. Furthermore, the dosage of the composition to be administered can be determined by performing experiments as is known to one of skill in the art.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Bacterial Strains, Plasmids and Culture Conditions

*Escherichia coli* XL-1 Blue (Stratagene) was used as the host for plasmid cloning and protein expression. Chromosomal DNA from *S. aureus* strain Newman was used to amplify the ClfA DNA sequence. All *E. coli* strains containing plasmids were grown on LB media with ampicillin (100 μg/ml).

EXAMPLE 2

Manipulation of DNA

DNA restriction enzymes were used according to the manufacturer's protocols (New England Biolabs) and DNA manipulations were performed using standard procedures (30) (Sambrook and Gething, 1989). Plasmid DNA used for cloning and sequencing was purified using the Qiagen Miniprep kit (Qiagen). DNA was sequenced by the dideoxy chain termination method with an ABI 373A DNA Sequencer (Perkin Elmer, Applied Biosystems Division). DNA containing the N-terminal ClfA sequences were amplified by PCR (Applied Biosystems) using Newman strain chromosomal DNA as previously described (31). The synthetic oligonucleotides (IDT) used for amplifying clfA gene products and for cysteine mutations are listed in Table I.

EXAMPLE 4

Expression and Purification of Recombinant Proteins

*E. coli* lysates containing recombinant ClfA and GST-Fg γ-chain fusion proteins were purified as previously described (35). PCR products were subcloned into expression vector pQE-30 (Qiagen) to generate recombinant proteins containing an N-terminal histidine (His) tag as previously described (9). The recombinant ClfA His-tag fusion proteins were purified by metal chelation chromatography and anion exchange chromatography as previously described (23). To generate recombinant $ClfA_{229-545}$ and $ClfA_{221-559}$ proteins, PCR-amplified fragments were digested with BamHI and KpnI and cloned into BamHI/KpnI digested PQE-30. The primers used to generate the recombinant constructs are listed in Table I. The reactions contained 50 ng of strain Newman DNA, 100 pmol of each forward and reverse primers, 250 nM of each dNTP, 2 units of Pfu DNA polymerase (Stratagene) and 5 ml Pfu buffer in a total volume of 50 ml. The DNA was amplified at 94° C. for 1 min, 48° C. for 45 sec; 72° C. for 2 min for 30 cycles, followed by 72° C. for 10 min. The PCR products were analyzed by agarose gel electrophoresis using standard methods (30) and purified as described above.

TABLE 1

| | | |
|---|---|---|
| ClfA229 | 5'-CCCGGATCCGGCACAGATATTACGAAT-3' | (SEQ ID NO: 1) |
| ClfA545 | 5'-CCCGGTACCTCAAGGAACAACTGGTTTATC-3' | (SEQ ID NO: 2) |
| For disulfide mutant: | | |
| rClfA327 | 5'-TGCTTTTACATCACATTTAGTATTTAC-3' | (SEQ ID NO: 3) |
| fClfA327 | 5'-GTAAATACTAAATGTGATGTAAAAGCA-3' | (SEQ ID NO: 4) |
| ClfA541 | 5'-CCCGGTACCTCAAGGAACAACTGGACAATCGAT ACCGTC-3' | (SEQ ID NO: 5) |
| Peptides: | | |
| Wild-type Fg γ 395-411 | GEGQQHHLGGAKQAGDV | (SEQ ID NO: 6) |
| Fg γ 395-411 D410A: | GEGQQHHLGGAKQAGAV | (SEQ ID NO: 28) |
| P16 -2Nt 397-411 | GQQHHLGGAKQAGAV | (SEQ ID NO: 7) |
| P16 -4Nt 399-411 | QHHLGGAKQAGAV | (SEQ ID NO: 8) |
| P16 -6Nt 401-411 | HLGGAKQAGAV | (SEQ ID NO: 9) |
| P16 -8Nt 403-411 | GGAKQAGAV | (SEQ ID NO: 10) |
| P16 -2Ct 395-409 | GEGQQHHLGGAKQAG | (SEQ ID NO: 11) |
| P16 -4Ct 395-407 | GEGQQHHLGGAKQ | (SEQ ID NO: 12) |

EXAMPLE 3

Construction of Disulphide Mutants (Stable Form of ClfA)

Cysteine mutations were predicted by comparing $ClfA_{221-559}$ to $SdrG_{(273-597)}$ disulfide mutant with stable closed conformations (32) and by computer modeling. A model of ClfA in closed conformation was built based on the closed conformation of the SdrG-peptide complex (25). The Cβ-Cβ distances were calculated for a few residues at the C-terminal end of the latch and strand E in the N2 domain. Residue pairs with Cβ-Cβ distance less than 3 Å were changed to cysteines to identify residues that could form optimum disulfide bond geometry. The D327C/K541C mutant was found to form a disulfide bond at the end of the latch. The cysteine mutations in $ClfA_{D327C/K541C}$ were generated by overlap PCR (33-34). The forward primer for PCR extension contained a BamHI restriction site and the reverse primer contained a KpnI restriction site. The mutagenesis primers contained complementary overlapping sequences. The final PCR product was digested with BamHI and KpnI and was ligated into same site in the expression vector pQE30 (Qiagen). All mutations were confirmed by sequencing. The primers used are listed in Table I.

EXAMPLE 5

Enzyme-linked Immunosorbent Assay

The ability of the wild-type $ClfA_{229-545}$ and disulfide ClfA mutants to bind Fg was analyzed by ELISA-type binding assays. Immulon 4HBX Microtiter plates (Thermo) were coated with human Fg (1 μg/well) in HBS (10 mM HEPES, 100 mM NaCl, 3 mM EDTA, pH 7.4) over-night at 4° C. The wells were washed with HBS containing 0.05% (w/v) Tween-20 (HBST) and blocked with 5% (w/v) BSA in HBS for 1 h at 25° C. The wells were washed 3 times with HBST and recombinant ClfA proteins in HBS were added and the plates were incubated at 25° C. for 1 h. After incubation, the plates were washed 3 times with HBST. Anti-His antibodies (GE Healthcare) were added (1:3000 in HBS) and the plates were incubated at 25° C. for 1 h. The wells were subsequently washed 3 times with HBST and incubated with Goat anti-mouse-AP secondary antibodies (diluted 1:3000 in HBS; Bio-Rad) at 25° C. for 1 h. The wells were washed 3 times with HBST and AP-conjugated polyclonal antibodies were detected by addition of p-nitrophenyl phosphate (Sigma) in 1 M diethanolamine (0.5 mM $MgCl_2$, pH 9.8) and incubated at 25° C. for 30-60 min. The plates were read at 405 nm in an ELISA plate reader (Themomax, Molecular Devices). For the inhibition assays, recombinant $ClfA_{229-545}$ was pre-incubated with Fg γ peptides in HBS for 1 h at 37° C. The recombinant protein-peptide solutions were then added to plates coated with 1 mg/well GST fusion protein containing the native human Fg γ 395-411 sequence (called GST-Fg $\gamma^{1-17}$) and bound protein was detected as described above. If the peptide binds ClfA it would inhibit binding of the GST-Fg $\gamma^{1-17}$ to the MSCRAMM.

EXAMPLE 6

Synthesis of Gamma Chain Peptides

The wild-type and mutated peptides corresponding to the 17 C-terminal residues of the fibrinogen γ-chain (residues 395-411) and truncated versions of this peptide (listed in Table I) were synthesized as previously described and purified using HPLC (9).

EXAMPLE 7

Isothermal Titration Calorimetry.

The interaction between ClfA proteins and soluble Fg peptides was analyzed by Isothermal titration calorimetry (ITC) using a VP-ITC microcalorimeter (MicroCal). The cell contained 30 mM ClfA and the syringe contained 500-600 mM peptide in HBS buffer (10 mM HEPES, 150 mM NaCl, pH 7.4). All samples were degassed for 5 min. The titration was performed at 30° C. using a preliminary injection of 5 ml followed by 30 injections of 10 ml with an injection speed of 0.5 ml/sec. The stirring speed was 300 rpm. Data were fitted to a single binding site model and analyzed using Origin version 5 (MicroCal) software.

EXAMPLE 8

Crystallization

The $ClfA_{D327C/K541C}$ protein was purified as described and concentrated to 30 mg/ml. The synthetic γ-chain peptide analogs, P16 and N-terminal truncations of P16 (P16-2Nt, P16-4Nt and P16-6Nt) were mixed with the protein at 1:20 molar ratio and left for 30 min at 5° C. This mixture was screened for crystallization conditions. Small needles of the ClfA/P16-2Nt, -4Nt and -6Nt were obtained during initial search of the crystallization condition, but we could only successfully optimize ClfA/P16-4Nt and ClfA/P16-6Nt. Diffraction quality crystals were obtained by mixing 2 μl of protein solution with 2 μl of reservoir solution containing 16-20% PEG 8K, 110 mM succinic acid pH 6.0.

EXAMPLE 9

X-ray Data Collection, Structure Solution and Refinement

Crystals of ClfA/P16-4Nt were flash frozen with a stabilizing solution containing 20% glycerol. Diffraction data were measured on Rigaku R-Axis $IV^{++}$ detector. A total of 180 frames were collected at a detector distance of 120 mm with 1° oscillation. Data were indexed, integrated and scaled using d*terk (47) (Pflugrath, 1999). The crystals diffracted to 1.95 Å and the data statistics were listed in Table 2. Calculation of the Matthews coefficient suggested the presence of 2 copies of the molecule in the unit cell of the triclinic cell. The structure was solved by molecular replacement (MR) with the program PHASER (36) using individual N2 and N3 domains of ClfA as search model. Solutions for the N3 domain were obtained for the two copies followed by the solutions of N2 domains. Data covering 2.5-15 Å were used for the molecular replacement solution. Electron density maps calculated during the initial rounds of refinement showed interpretable density for 11 out of 13 peptide residues in both the copies of the complex. Modeling building of the peptide and rebuilding of a few loop regions were performed using the program COOT (37). A few cycles of ARP/WARP (38) were performed to improve the map and for the building of water model. After a few cycles of refinement using Refmac5.0 (39), electron density was clear for only the backbone atoms for two remaining N-terminal residues of the peptide molecule D and one residue for peptide C. The final model of ClfA included residues 230-299, 303-452, 456-476 and 479-545 in molecule A and 230-438, 440-476 and 479-542 in molecule B. The structure was refined to a final R-factor of 20.9% and R-free of 27.8%. Stereochemical quality of the model was validated using PROCHECK (40).

TABLE 2

Crystallographic data measurement and refinement data

| | |
|---|---|
| Cell dimensions | |
| a, b, c (Å) | 35.43, 61.84, 81.78 |
| α, β, γ (°) | 85.44, 81.84, 82.45 |
| Space group | P1 |
| Resolution (Å) | 1.95-15.0 |
| Reflections total/unique | 86051/46090 |
| Completeness (%) | 93.9 |
| $R_{merge}$ * | 0.074 |
| Number of molecules in the asymmetric unit | 2 |
| Rfactor/$R_{free}$ + | 0.211/0.279 |
| Bond rms deviation (Å) | 0.015 |
| Angle rms deviation (°) | 1.64 |
| Average B value (Å) | 29.9 |
| No of non-hydrogen atoms | 5226 |
| Protein | 4558 |
| Peptide | 141 |
| Water | 527 |
| Rms deviations from ideal values | |
| Bond lengths (Å) | 0.22 |
| Bond Angles (°) | 1.95 |
| PDB ID | 2vr3 |

* $R_{merge} = \Sigma|I_j - \langle I \rangle|/\Sigma I_j$; where $I_j$ is the measured and ⟨I⟩ is the mean intensity of reflection hkl;
+ $R_{free}$ is calculated over 2% of randomly selected reflections not included in the refinement.

EXAMPLE 10

Integrin ($a_{IIb}b_3$) Inhibition Assay

For $\alpha_{IIb}\beta_3$ inhibition assay. $\alpha_{IIb}\beta_3$ Immulon 4HBX Microtiter 96-well plates (Thermo) were coated with $a_{IIb}b_3$ (0.25 mg/well) in TBS (25 mM Tris, 3 mM KCl, 140 mM NaCl, pH 7.4) over night at 4° C. The wells were washed with TBS containing 0.05% (w/v) Tween-20 (TBST). After blocking with 3% (w/v) BSA dissolved in TBS for 1 h at RT, 10 nM of full length Fg was applied in the presence of either WT $\gamma^{1-17}$, $\gamma^{1-17}{}_{D16A}$ or $\gamma^{1-17}{}_{K12A}$ peptides and plates were incubated at RT for another hour. The bound full length Fg was then detected by goat anti human Fg (1:1000 dilution, Sigma) antibody followed by horseradish peroxidase-conjugated rabbit anti-goat IgG antibody (1:1000 dilution, Cappel). After incubation with 0.4 mg/ml of substrate, o-phenylenediamine dihydrochloride (OPD, Sigma) dissolved in phosphate-citrate buffer, pH 5.0, bound antibodies were determined in an ELISA reader at 450 nm. The proteins, antibodies and peptides were diluted in TBST containing 1% (w/v) BSA, 2 mM $MgCl_2$, 1 mM of $CaCl_2$ and $MnCl_2$.

EXAMPLE 11

Molecular Modeling

All molecular modeling studies were performed using InsightII software (Accrelys Inc). Modeling of FnbpA-peptide complex was performed using "Homology" module available in InsightII using $ClfA_{229-545}$ peptide complex as a template. Prior to model building, the amino acid sequence of $ClfA_{229-545}$ was aligned with FnbpA (GENBANK® ID: CA077272) using Lalign (41). The aligned sequences were manually checked for any gaps in the core β-sheet forming regions of ClfA. The final model was subjected to molecular dynamics simulation followed by conjugate gradient energy minimization. Figures were made using RIBBONS (42). The atomic coordinates and structure factors of the complex structure have been deposited in Protein Data Bank with accession number 2vr3.

EXAMPLE 12

Identification of Critical Residues in Fg Required for Binding to ClfA

In previous studies, a segment of ClfA composed of residues 221-559 was shown to bind to the C-terminal end of the human Fg γ-chain (9). Based on structural similarities with SdrG, a smaller ClfA construct (229-545) predicted to be composed only of the N2 N3 domains was designed and it was shown that $ClfA_{229-545}$ retained the Fg-binding activity. To identify specific residues in Fg that are important for binding to $ClfA_{229-545}$, a panel of peptides (FIG. 1A; SEQ ID NOS: 13-29) based on the Fg γ-chain sequence 395-411 (referred to as $g^{1-17}$) were synthesized in which each position was sequentially substituted with an alanine residue (alanines 11 and 14 changed to serines). These peptides were tested as inhibitors in solid-phase binding assays. Peptides $g^{1-17}{}_{H6A}$, $g^{1-17}{}_{H7A}$, $g^{1-17}{}_{G10A}$, $g^{1-17}{}_{Q13A}$, $g^{1-17}{}_{A14S}$ and $g^{1-17}{}_{G15A}$ were significantly less potent inhibitors than the native sequence suggesting that the Fg residues H6, H7, G10, Q13, A14 and G15 interact with ClfA (FIG. 1B). Remarkably, peptides $g^{1-17}{}_{A11S}$, $g^{1-17}{}_{D16A}$ and $g^{1-17}{}_{V17A}$ showed an enhanced inhibition of ClfA binding to a recombinant form of residues 395-411 of the Fg g chain fused to a GST protein (GST-Fg $g_{1-17}$) compared to a peptide with the wild-type sequence, indicating a higher affinity of the peptide variants for ClfA.

Figure 1D:
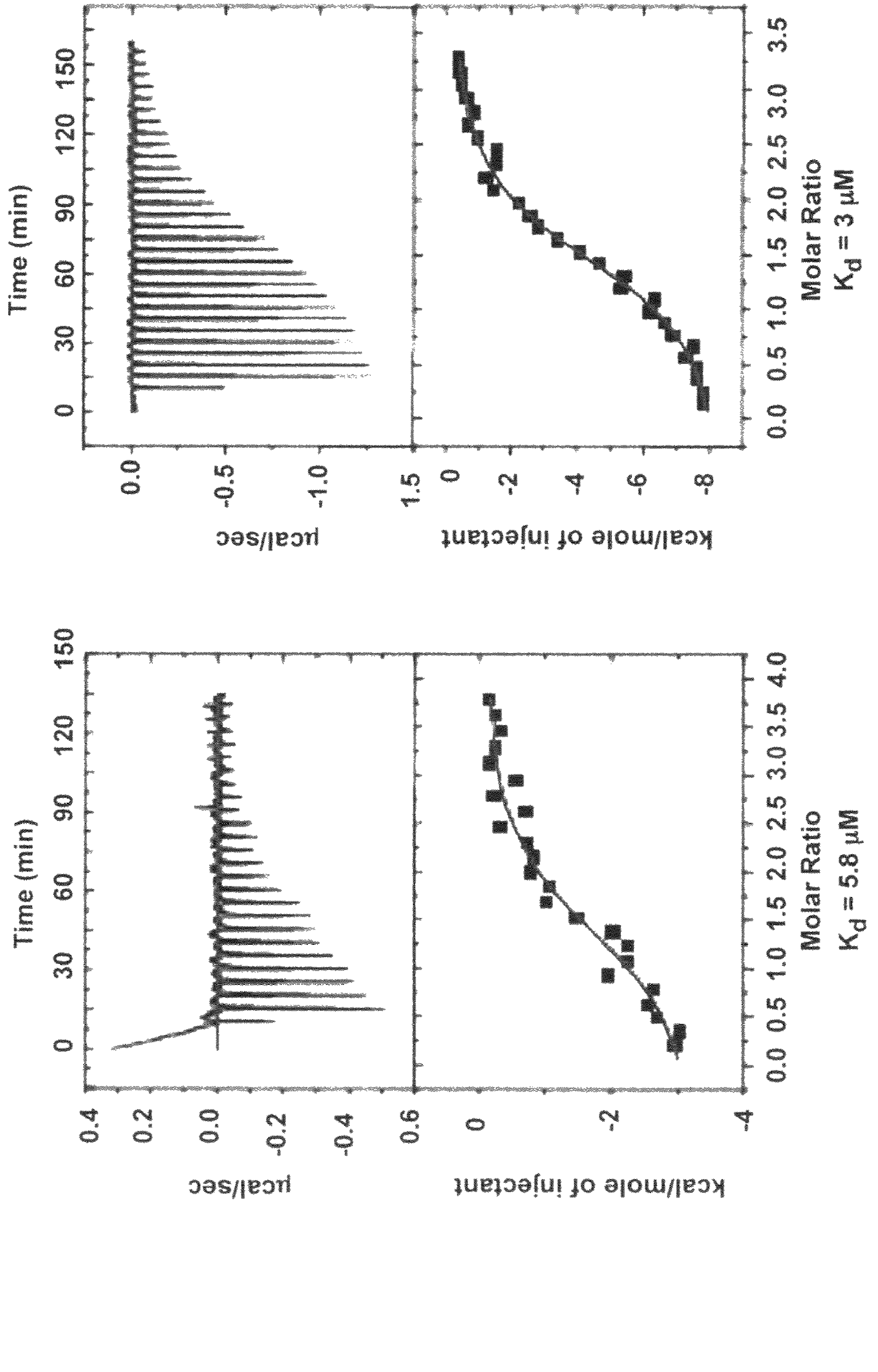

The ability of $ClfA_{229-545}$ to bind to the peptide containing the $g^{1-17}{}_{D16A}$ mutation was further characterized. In solid-phase assays, ClfA binds to immobilized GST-Fg $g^{1-17}$ fusion protein with a lower affinity ($K_d$=657 nM) compared to the mutated GST-Fg $g^{1-17}{}_{D16A}$ ($K_d$=35 nM) (FIG. 1C). In solution, using isothermal titration calorimetry (ITC) assays, (FIG. 1D), ClfA also binds with a lower affinity to the native $g^{1-17}$ peptide ($K_d$ of 5.8 mM) compared to the mutant Fg $g^{1-17}{}_{D16A}$ ($K_d$ of 3 mM). Thus, although the apparent dissociation constants differ according to the assays used to estimate them, similar trends in affinity between the wild-type and the D16A mutation were observed. It is currently unknown why the difference between the $K_d$s was much greater in the solid phase binding assays compared to the ITC analysis.

The present invention demonstrates that alanine substitution at the C-terminal region of the peptide affected MSCRAMM binding suggesting that the ClfA binding site is located at the very C-terminus of the Fg γ-chain (FIGS. 1A-1D). Results also show that certain amino acid changes in the $g^{1-17}$ sequence enhance ClfA binding compared to the wild-type Fg sequence indicating that the human Fg γ C-terminal 17 residues may not be the optimum ligand for ClfA.

Figures 2A, 2C:
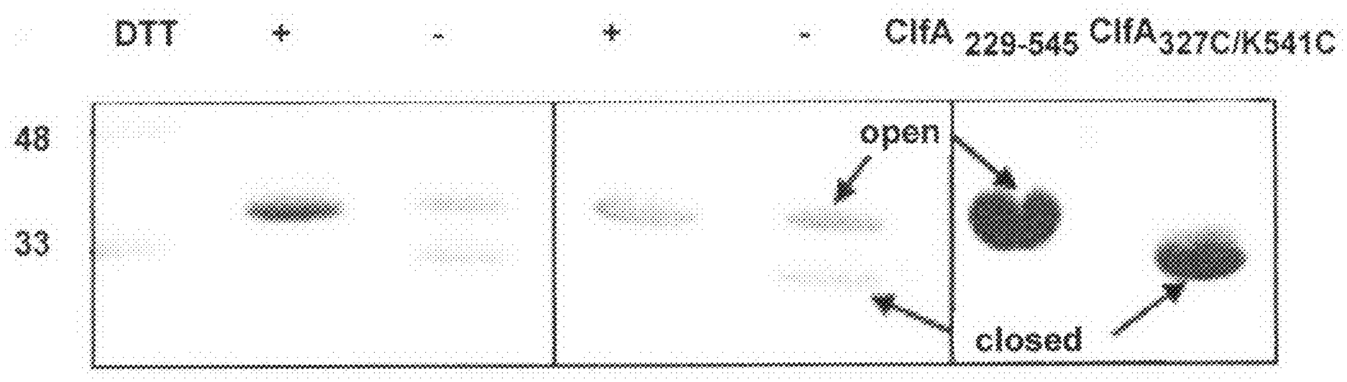
FIGS. 2A-2D illustrate Fg and Fg γ P16 peptide truncations binding to different forms of ClfA.
Figure 2B:
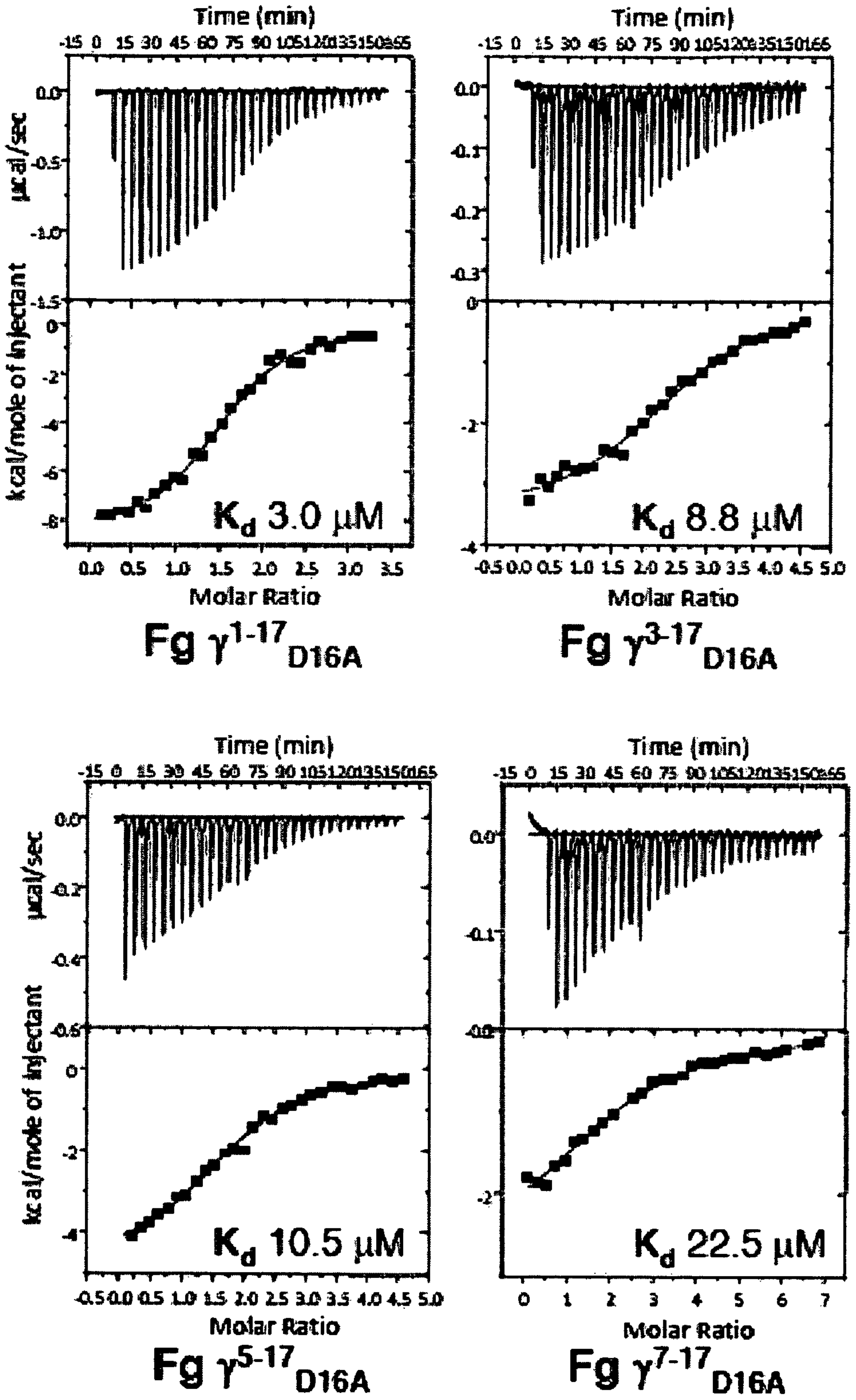
Figure 2D:
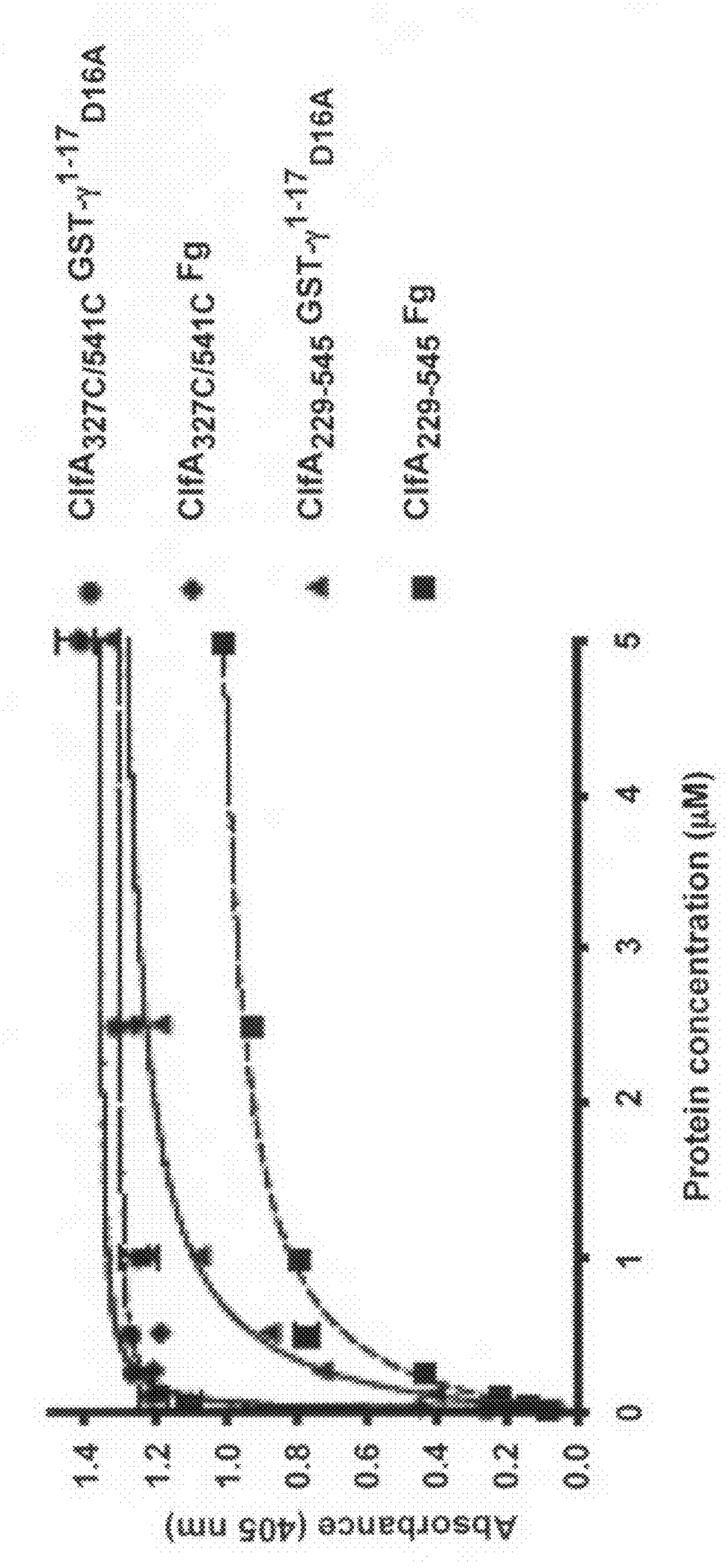

Analysis of the previously solved SdrG-Fg peptide complex crystal structure showed that only 11 out of the 18 peptide residues interacted with the MSCRAMM. Similarly, only a part of the 17-residue sequence may be required for binding to ClfA. In order to establish the minimum Fg peptide required for binding to $ClfA_{229-545}$, a series of N- and C-terminal truncations of the $g^{1-17}{}_{D16A}$ peptide were synthesized (FIG. 2A; SEQ ID NOS: 7-12 & 28). Truncations of 2, 4, 6 or 8 amino acids at the N-terminus of the Fg g-peptide resulted in a reduced but detectable binding affinity when tested using ITC. There was a direct relationship between the length of the peptide and its affinity for ClfA. The smaller the peptide, the lower was the observed affinity for the MSCRAMM (FIG. 2B). Thus, the N-terminal residues of the Fg peptide (residues 1-8) may either contribute to or stabilize the binding of the peptide to ClfA, but are not critical for the interaction. On the other hand, deletions of 2 or 4 residues from the C-terminal end of the $g^{1-17}{}_{D16A}$ peptide abolished binding (data not shown). These results indicate that the C-terminal amino acids of Fg are critical for binding to ClfA; these data correlate with a previous report that showed that Fg lacking the C-terminal residues AGDV in the g chain (corresponding to residues 14-17 in the peptide) or a variant that replaces the last four g-chain residues with 20 amino acids lacks the ability to bind recombinant $ClfA_{221-550}$ and or to induce *S. aureus* clumping (9).

EXAMPLE 13

A Stabilized Closed Confirmation of $ClfA_{229-545}$ Binds Fg with a Higher Affinity than the Open Form The Fg binding mechanism of $SdrG_{276-596}$ involves a transition from an open conformation, where the peptide binding trench between the N2 and N3 domains is exposed for ligand docking, to a closed conformation of the $SdrG_{276-596}$ in complex with the ligand. The insertion of the N3 extension into the latching trench on N2 stabilizes the closed conformation (32). The closed conformation of apo SdrG N2N3, stabilized by introducing a disulfide bond between the end of the N3 latch and the "bottom" of N2, no longer binds Fg (32) demonstrating that the dynamics of the latch is critical for the SdrG ligand interaction. To explore if the binding of ClfA to Fg is also dependent on a movement of the latch, a ClfA construct containing two cysteine substitutions was constructed. The locations of the cysteine mutations were determined using computer modeling and by sequence alignment to corresponding mutations in SdrG (32). The mutant $ClfA_{D327C/K541C}$ generated a stable, closed conformation form. This recombinant His-tag fusion protein was purified by $Ni^+$ chelating chromatography; ion-exchange and gel permeation chromatography. The $ClfA_{D327C/K541C}$ open and closed conformation forms were examined by SDS-PAGE analysis (FIG. 2C).

Under non reducing conditions, the disulfide bonded closed form of $ClfA_{D327C/K541C}$ migrated faster on SDS-PAGE than its non-disulfide bonded open form. Presumably, under non-reducing conditions, closed conformation mutants are more compact and migrate faster on SDS-PAGE than open conformation constructs. Under reducing conditions, the disulfide mutant and the wild-type protein migrate at the same rate. Surprisingly, the disulfide mutant $ClfA_{D327C/K541C}$ was able to bind Fg both in the open and closed conformations (FIG. 2C). Elisa-type binding assays where Fg or GST Fg $\gamma^{1-17}$ peptide were coated in microtiter wells and incubated with ClfA showed that the closed conformation $ClfA_{D327C/K541C}$ bound the ligand with a much lower apparent $K_d$ (34 nM Fg; 20 nM GST-Fg $\gamma^{1-17}$) compared to the wild-type $ClfA_{229-545}$ (apparent $K_d$ 305 nM Fg; 222 nM GST-Fg $\gamma^{1-17}$) (FIG. 2C). These results demonstrate that an open conformation may not be required for Fg binding to ClfA and that Fg binding by ClfA involves a mechanism that is different from the DLL mechanism employed by SdrG.

EXAMPLE 14

Figure 3A:
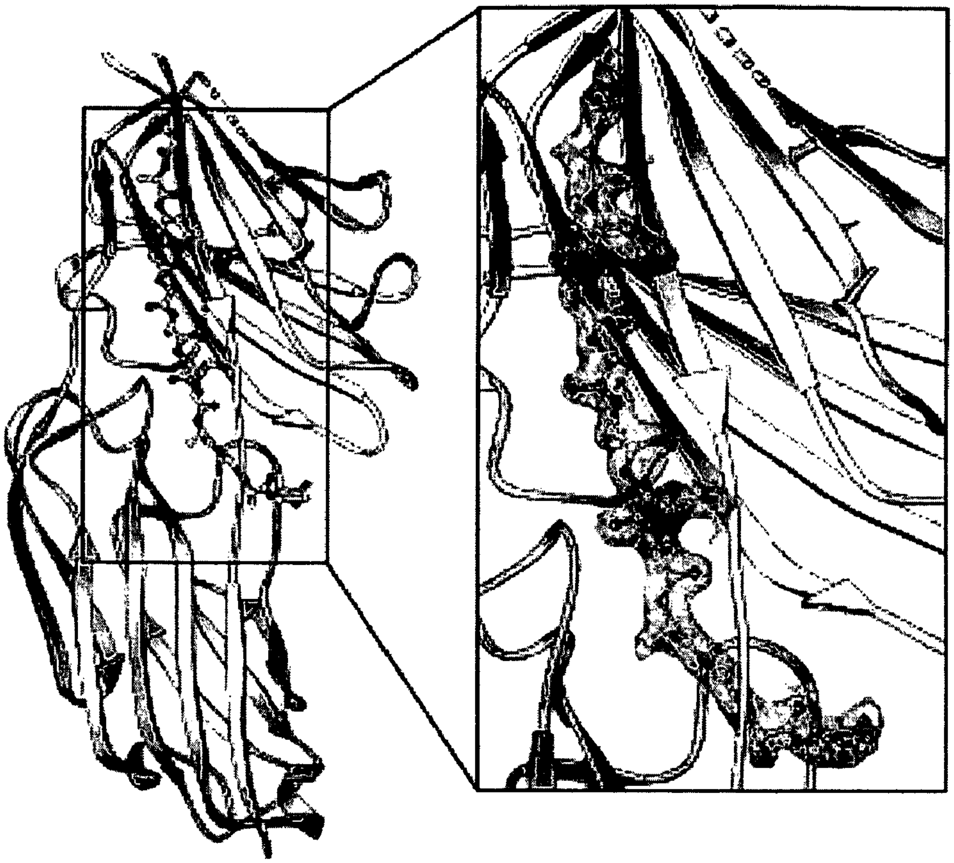
FIGS. 3A-3D are a representation of $ClfA_{D327C/K541C}$ (N2-N3)-peptide complex.
Figure 3B:
Figure 3C:
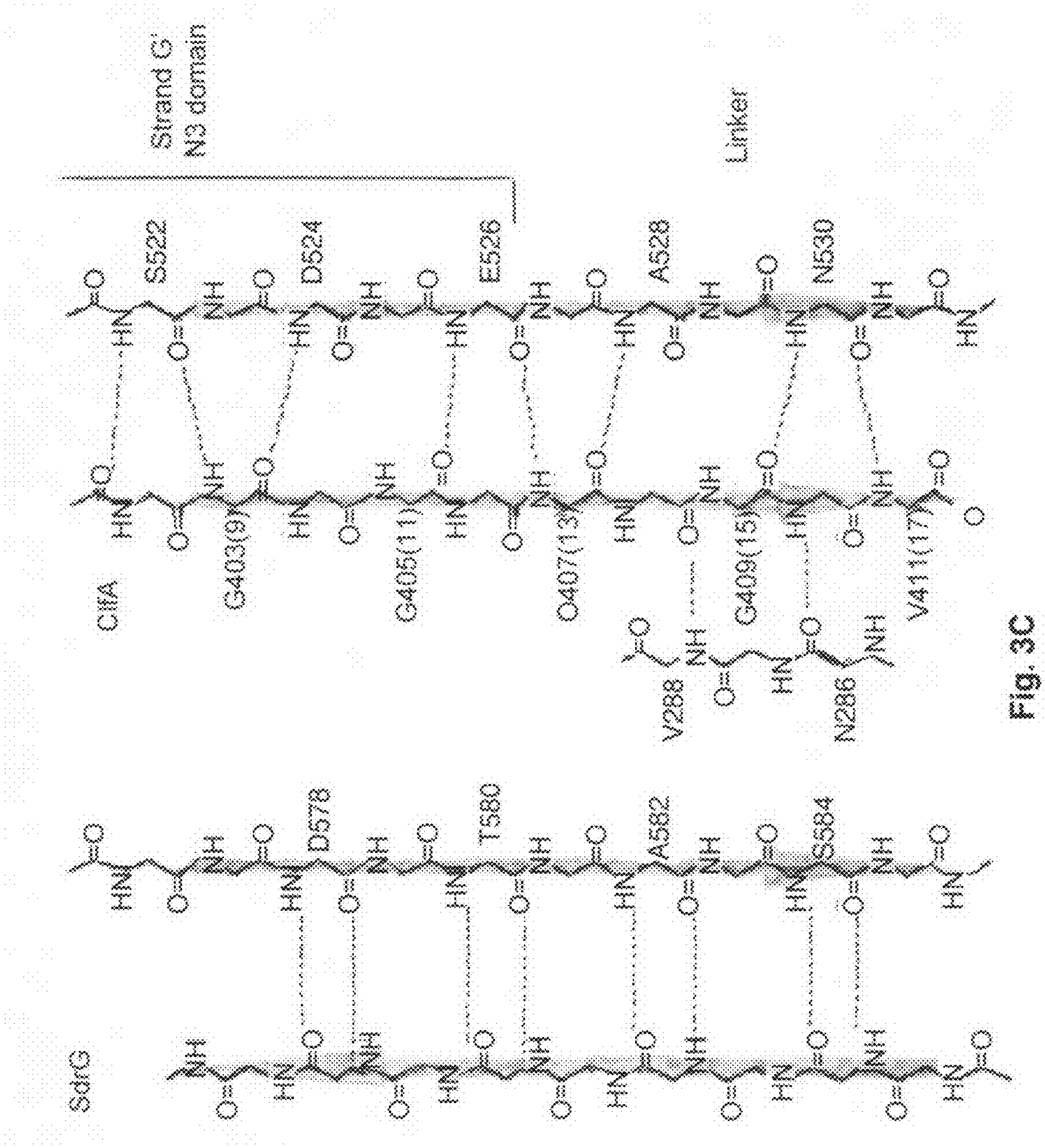
Figure 3D:
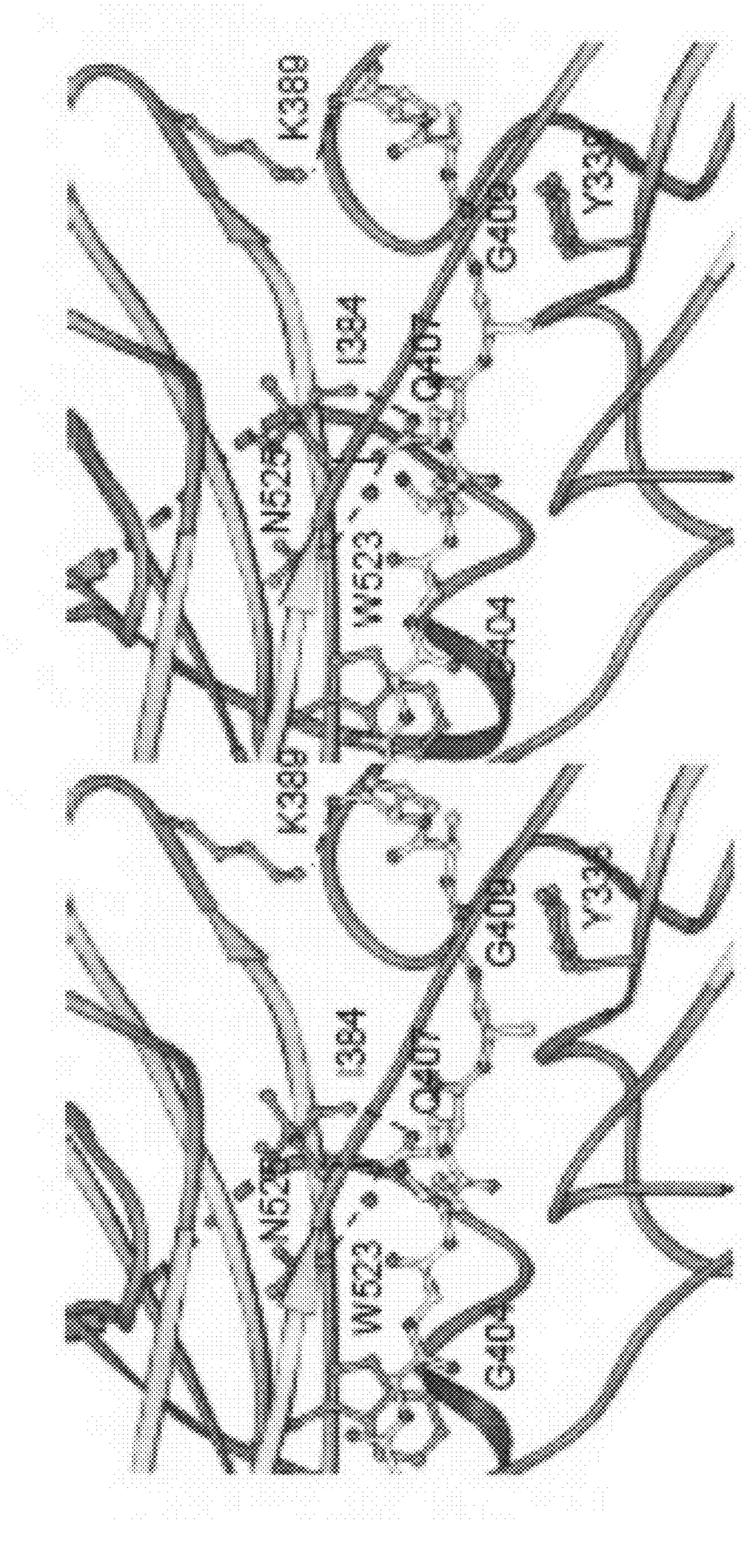

Crystal Structure of $ClfA_{(229-545)/D327C/K541C)}$ in Complex with a 13-Residue Fg-derived Peptide Crystallization screens were carried out with $ClfA_{D327C/K541C}$ in complex with several N-terminal truncations of the $g^{1-17}{}_{D16A}$ peptide that were shown to bind the MSCRAMM. Crystals of the stable closed conformation of $ClfA_{229-545}$ in complex with several peptides were obtained, but structure determination was attempted for only the $ClfA_{(229-545)D327C/K541C}$-$g^{5-17}{}_{D16A}$ peptide. The crystals of the ClfA-peptide complex diffracted to a 1.95 Å resolution. Two copies of ClfA-peptide complex were found in the asymmetric part of the unit cell and are referred to as A:C and B:D. Although the 13 residues of the Fg $g^{5-17}$ chain synthetic peptide were used for crystallization, only 11 residues were completely observed in both copies. The two molecules of $ClfA_{D327C/K541C}$ (A and B) are nearly identical with rms deviation of 0.3 Å for 312 Cα atoms and 0.55 Å for backbone atoms. As observed in the apo-$ClfA_{221-559}$ structure, the $ClfA_{(229-545)D327C/K541C}$ N2 and N3 domains adopt a DE-variant IgG fold (24). The overall structure of the $ClfA_{D327C/K541C}$ peptide complex (A:C) and the two copies of the complexes A:C and B:D superimposed are shown in FIGS. 3A and 3B, respectively. The C-terminal extension of the N3 domain makes a β-sheet complementation with strand E of the N2 domain. This conformation is locked by the engineered disulfide bond as predicted by SDS-PAGE analysis (FIG. 2C) and confirmed by the crystal structure. The two copies of the Fg γ-peptide molecules are nearly identical with rms deviation of 0.5 Å for 11 Cα atoms and 0.89 Å for backbone atoms. The interaction between the $ClfA_{D327C/K541C}$ and the peptide buries a total surface area of 1849 $Å^2$ and 1826 $Å^2$ in the A:C and B:D complex, respectively. The interaction of the peptide with the N2 domain is predominantly hydrophobic in nature, in addition to a few main-chain hydrogen bonds (FIG. 3C). Interactions between the Fg peptide and the N3 domain are both hydrophobic and electrostatic with the electrostatic contribution coming almost entirely from the main chain-main chain hydrogen bonds due to the parallel β-sheet formation of the peptide with strand G of the N3 domain (FIG. 3C). The side-chain interactions between the peptide and ClfA are predominantly hydrophobic. The 11 C-terminal residues of the Fg g-chain peptide sequence that interact with ClfA are composed of only two polar residues, Lys12 and Gln13. Side chain atoms of Lys12 point away and do not interact with the ClfA protein whereas Gln13 makes two hydrogen bonds with the main chain atoms of Ile 384 in ClfA (FIG. 3D). A water-mediated interaction is also observed between Gln13 of the peptide and Asn525 of ClfA. Tyr338 in the N2 domain and Trp523 in the N3 domain play an important role in anchoring the peptide molecule. Tyr338 and Trp523 are stacked with residues Gly15 and Gly10, respectively. In addition, Met521 and Phe529 make hydrophobic interactions with Ala7 and Val17, respectively. The C-terminal residues of the peptide Ala14, Gly15, Ala16, and Val17 are buried between the N2-N3 domain interface with the terminal Val residue, presumably threaded through a preformed ligand binding tunnel after $ClfA_{D327C/K541C}$ adopted its closed conformation. A hydrogen bond is observed between Lys389 of ClfA and the C-terminal carboxyl group of the peptide (FIG. 6B).

EXAMPLE 15

Figure 4A:
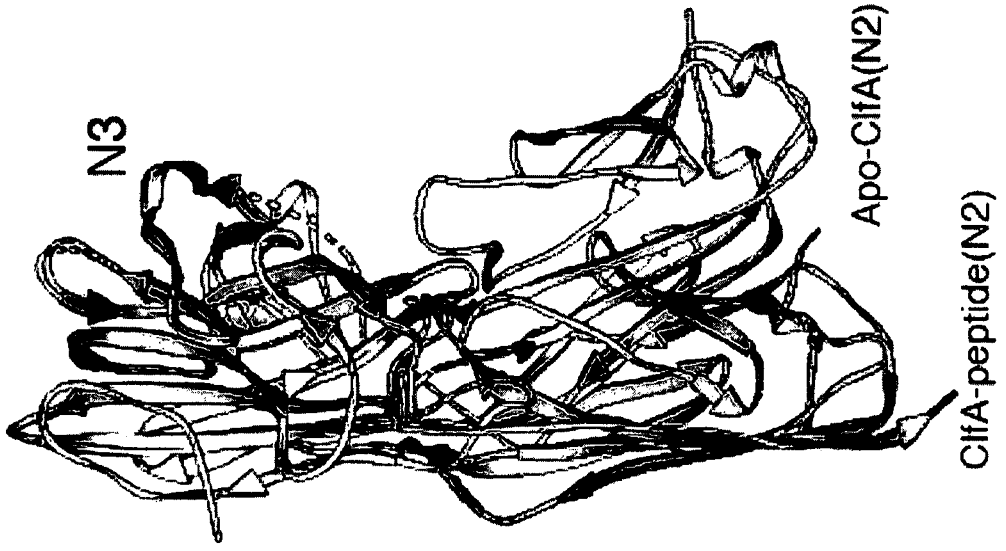
FIGS. 4A-4C illustrate the superposition of apo-ClfA, ClfA-peptide and SdrG-peptide structures.

Structural Differences Between the Closed Confirmation $ClfA_{(D327C/541C)}$-Peptide Complex and the Apo-$ClFA_{221-559}$ Protein The individual N2 and N3 domains in the apo-$ClfA_{221-559}$ and the closed form of $ClfA_{D327C/K541C}$ are almost identical with rms deviations of 0.33 and 0.42 Å for molecule A and 0.35 and 0.42 Å for molecule B, but the relative orientation of the N2 and N3 domains are significantly different (FIG. 4A). This difference affects the association of the N2 and N3 domains. In the apo conformation, the buried surface area between the N2 and N3 domains is 87 $Å^2$ compared to 367 $Å^2$ in the closed form of the $ClfA_{(221-559)D327C/K541C}$-peptide complex. In the apo-$ClfA_{221-559}$, the C-terminal residues (Ala528-Glu559) of the N3 domain fold back and do not interact with the N2 domain.

Figure 4B:
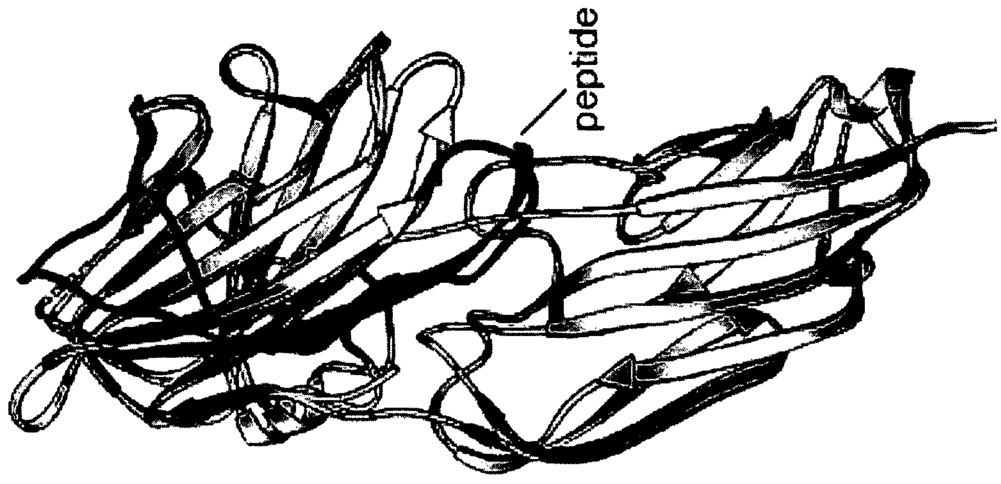

To understand if the altered N2-N3 orientation of the apo-form of ClfA (FIG. 4A) is due to the folded-back conformation, a model of the apo-$ClfA_{221-559}$ was constructed with the folded-back N3 domain and the N2 domain adopting an N2-N3 orientation similar to that observed in the closed form of the ClfA-peptide complex. This model shows that Tyr338 in the N2 domain makes severe clashes with residues Ser535 and Gly534 of the folded back segment. An alternate conformation for these residues is unlikely due to spatial constraints. Thus, it is unlikely that the two domains in the folded-back conformation could adopt an orientation similar to their orientation in the ClfA-peptide complex. Moreover the folded-back segment completely occupies the binding site (FIG. 4B). Therefore, in the folded-back conformation, the ligand binding site appear not to be accessible to the peptide.

It is presently unclear what the spatial rearrangements of the N2N3 domains are in intact ClfA expressed on the surface of a staphylococcal cell. The two structures of these domains solved so far where one is active and the other inactive provide a structural basis for the possible regulation of ClfA's Fg binding activity by external factors. One such factor may be $Ca^{2+}$ which has been shown to inhibit ClfA-Fg binding (O'Connell et al., 1998). Alternatively, it is possible that the folded-back conformation (which is a larger protein construct) is only one of the many possible conformations adopted by the unbound protein. Most likely, MSCRAMMs proceed from the unbound to the bound forms in a very dynamic mechanism where different intermediate forms could be achieved.

EXAMPLE 16

Figure 4C:
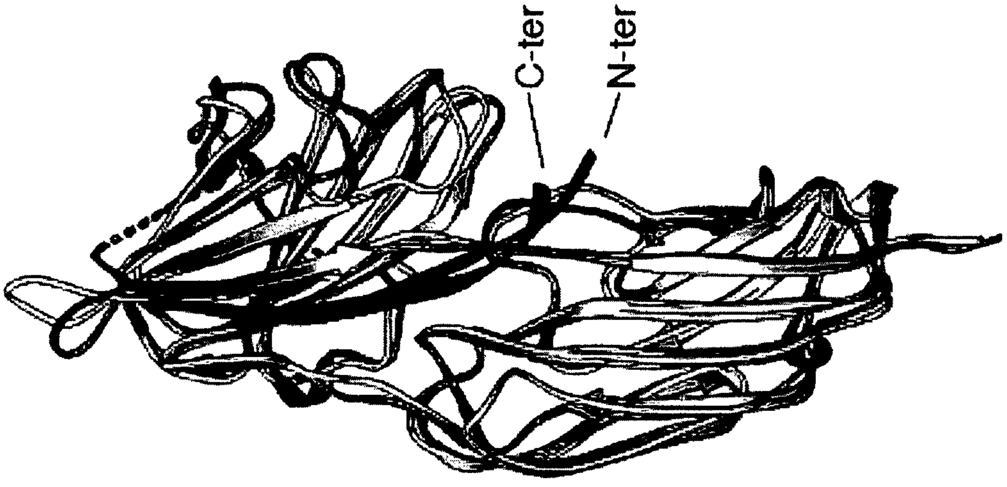

Structural Similarities/differences Between the Closed Form of the ClfA-peptide and SdrG-peptide Complexes The major difference between Fg-binding to ClfA and SdrG is that the directionality of the bound ligand peptide is reversed (FIG. 4C). The C-terminal residues of the ligand is docked between the N2 and N3 in ClfA and makes a parallel β-sheet complementation with strand G of the N3 domain, whereas in SdrG, the N-terminal residues of the ligand are docked between the N2 and N3 domains and form an anti-parallel β-sheet with the G strand. In both cases there are 11 ligand residues that make extensive contact with the MSCRAMM but with one residue shift towards the N3 domain in ClfA. Of these 11 residues, 7 and 11 residues participate in the β-strand complementation of SdrG and ClfA, respectively. Although the peptide binding model of ClfA is different to that of SdrG, the inter-domain orientations of the two MSCRAMMS are very similar (25). Superposition of 302 corresponding atoms in the N2 and N3 domains of ClfA and SdrG showed a small rms deviation of 0.65 Å indicating the high structural similarity between the two MSCRAMMS. Another striking difference is that ClfA does not require an open-conformation for ligand binding, whereas Fg cannot bind to a stabilized closed conformation of SdrG. ClfA binds the C-terminal end of Fg and the last few residues of the γ-chain can be threaded in to the binding pocket. In the SdrG-Fg interaction, the binding segment in Fg does not involve the seven N-terminal residues of the ligand and therefore an open conformation is required for ligand binding.

EXAMPLE 17

A Structural Model for Fg Binding to FnbpA

Figure 7A:
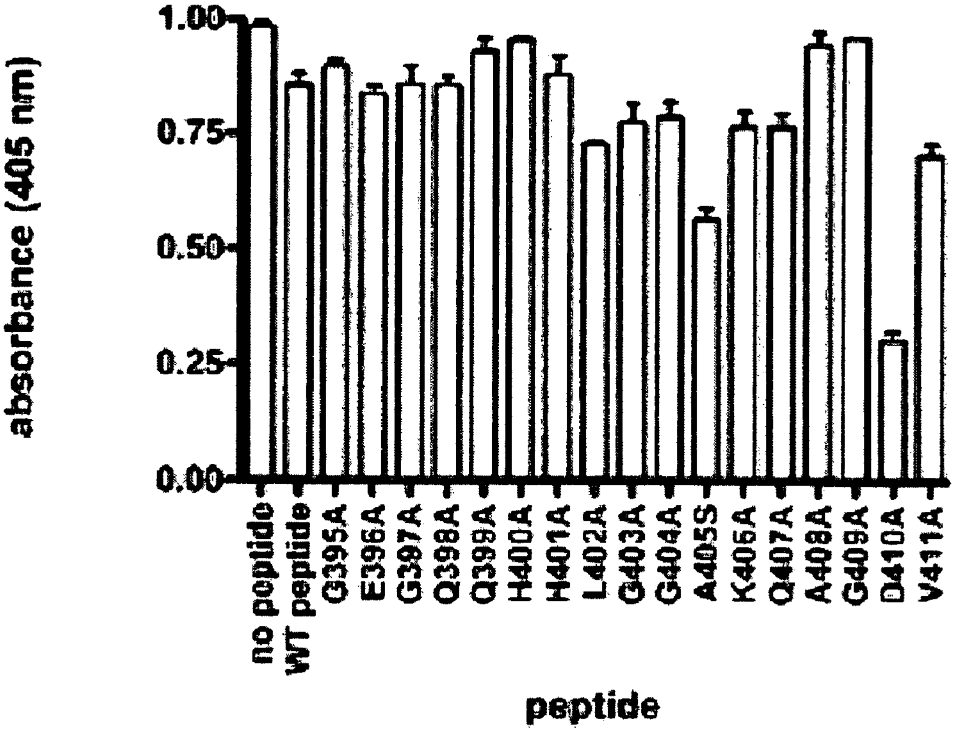
FIGS. 7A-7B illustrate FnbpA binding to GST-Fg γ chain peptides.
Figure 7B:

FnbpA, like ClfA, has been shown to bind the Fg γ-chain at the C-terminus. The panel of peptides with alanine substitutions (FIG. 1A) was tested as inhibitors of FnpA binding to Fg in a solid phase assay. The pattern of inhibition was similar to that measured for ClfA (FIG. 7A). In addition, earlier mutational studies on FnbpA showed that two residues, N304 and F306, were required for full Fg binding (43). The corresponding residues in ClfA are P336 and Y338. Tyr 338 plays a key role in anchoring Gly15 of the γ-chain peptide. Together, these results indicate that the FnbpA Fg binding mechanism could be similar to that of ClfA. The availability of the now determined ClfA-peptide complex prompted us to model an FnbpA-Fg complex (FIG. 7B). The homology model of the FnbpA-peptide complex showed that FnbpA can adopt a structure similar to that of the ClfA-ligand complex. Although there is only 25% sequence identity between ClfA and FnbpA, this model shows that almost 50% of the residues that interact with the γ-chain peptide are conserved between FnbpA and ClfA and many others are similar. Together, the binding data and the modeling studies suggest that ClfA and FnbpA bind Fg by a similar mechanism.

EXAMPLE 18

Species Variations in Fg-binding to ClfA

Figure 5A:
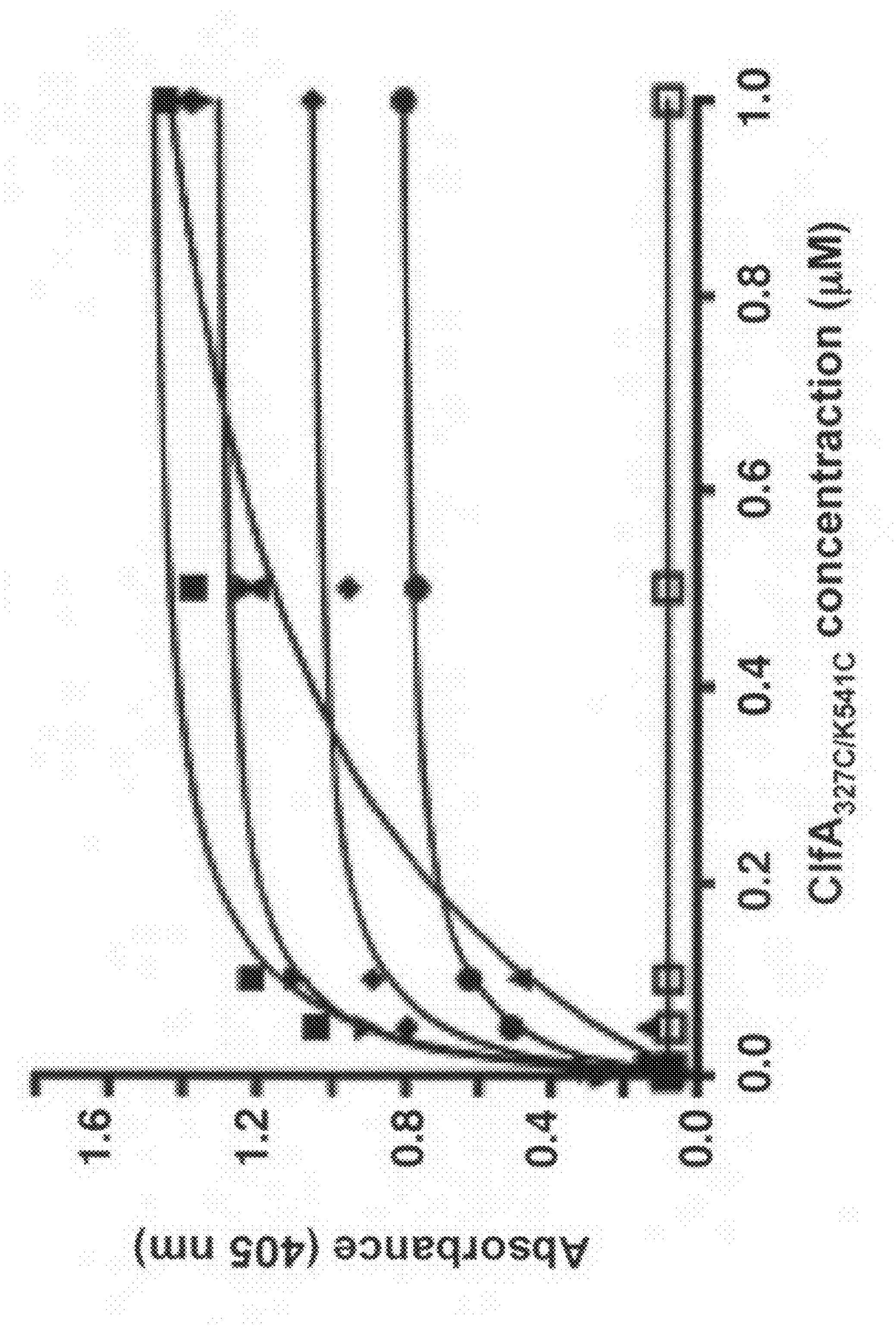
FIGS. 5A-5C illustrate species specificity of ClfA-Fg binding.
Figure 5B:
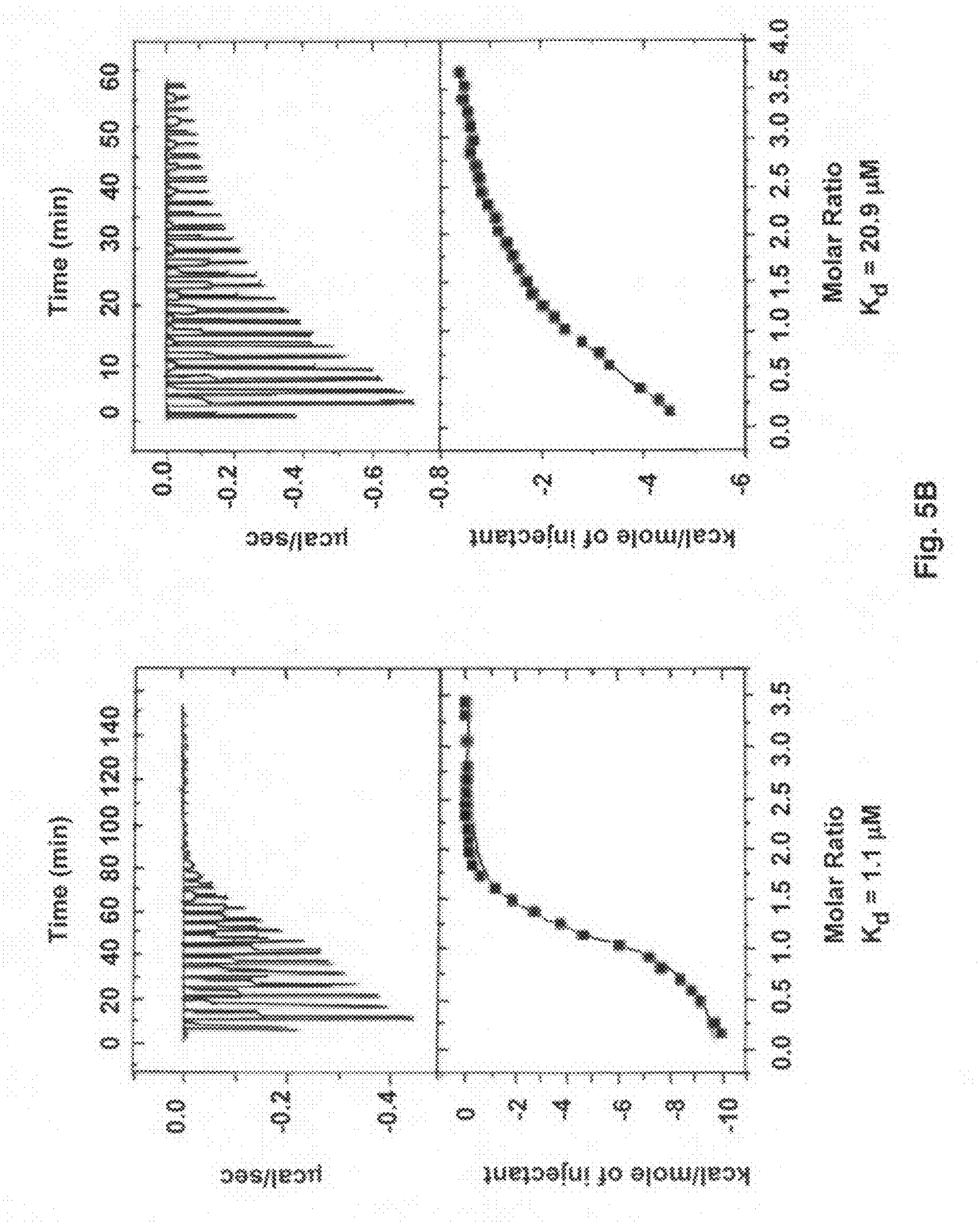
Figure 5C:
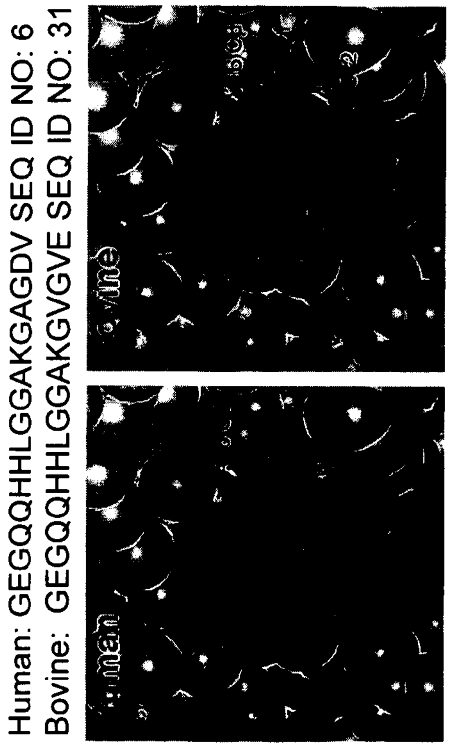

There is a significant variation in the C-terminal sequences of the Fg g-chain among different animal species. The binding of $ClfA_{327C/541C}$ to Fg isolated from different animal species was explored using a solid-phase binding assay. $ClfA_{327C/541C}$ binds bovine Fg with significantly lower apparent affinity than human Fg; binding of the MSCRAMM to sheep Fg could not be detected (FIG. 5A). The bovine Fg γ sequence is available and the binding data obtained in the ELISA type assay was corroborated by measuring the affinity of $ClfA_{327C/541C}$ for the Fg $g^{1-17}_{D16A}$ peptide and a peptide representing the bovine Fg γ chain sequence using ITC (FIG. 5B). A closer examination of the ClfA-peptide interaction and the sequence variations between the human and the bovine Fg γ-chain C-terminal segment suggests that two of the four amino acid variations, at positions 14 and 16, could potentially explain the difference in the affinity (FIG. 5C Upper panel). In the ClfA-peptide crystal structure, Ala14 and Ala16 are completely buried between the N2 and N3 domains (binding trench). Replacement of Ala with Val at either position would impose steric conflicts between ClfA and Fg. However, Asp, and not Ala, is the natural sequence at position 16 of the peptide in human Fg. Modeling shows that Asp could adopt a conformation that could allow the side chain to point towards the solvent with minimal steric conflict with the ClfA. The less bulky Ala would fit better in the binding site than Asp, which explains the higher affinity of ClfA for the $\gamma^{1-17}_{D16A}$ peptide compared to the WT peptide. Valine is branched at the Cβ atom and this residue would make steric clashes with the residues lining the binding trench in ClfA independent of the side-chain conformation of the Val residue. The other two non-contributing variations in the bovine compared to the human Fg sequence are His6→Gln and Val17→Glu. The electron density for the side chain of His6 in the peptide is not interpretable indicating that the side-chain of the His6 and its corresponding residue, Gln, in bovine Fg do not participate significantly in the interaction. Molecular modeling shows that even a bulkier Glu residue instead of Val at this position 17 is unlikely to sterically clash with ClfA. Therefore H→Q and V→Q variations at positions 6 and 17 may not contribute to the difference in affinity. A specific linear sequence often appears to be recognized by a staphylococcal MSCRAMM, which raises the possibility that the MSCRAMMs can differentiate between the ligand analogs from different species. This hypothesis is illustrated herein where it can also explain in structural terms the preferential binding of ClfA to human over bovine fibrinogen. The observed species specificity of MSCRAMM ligand interaction potentially could contribute to the observed species tropism of many staphylococcal strains.

EXAMPLE 19

Comparison of Fg Binding to ClfA and the Platelet Integrin $\alpha_{IIb}\beta_3$ The C-terminus of Fg γ-chain, which is targeted by ClfA, is also important for platelet aggregation mediated by the $\alpha_{IIb}\beta_3$ integrin, a vital step in thrombosis (9, 44). The Fg γ-chain complex with $\alpha_{IIb}\beta_3$ structure is not available but structures of related complexes provide clues on how $\alpha_{IIb}\beta_3$ likely interact with Fg (45). In addition, the crystal structure of the $\alpha_v\beta_3$ integrin in complex with an RGD ligand provided a structural model of a similar ligand-integrin interaction (46). In this structure, the Asp (D) residue of the RGD sequence coordinates with the metal ion in the Metal Ion Dependent Adhesion Site (MIDAS) of the integrin and thus plays a key role in the interaction. The platelet specific integrin $\alpha_{IIb}\beta_3$ recognizes ligands with an RGD sequence or the sequence Lys-Gln-Ala-Gly-Asp-Val (SEQ ID NO: 30) found in Fg (45). Structural studies with drug molecules that antagonize the integrin-RGD or -Fg interaction showed that each of the drug molecules contains a carboxyl group moiety that mimics the aspartic acid and a basic group that mimics the Arg (or Lys in the case of Fg) in the ligand (45). These results suggest that the Lys and Asp residues in the C-terminal γ-chain sequence are critical for the interaction with integrin. Interestingly, the present invention shows that these Lys and Asp residues in Fg are not critical for ClfA binding (FIG. 1B). In fact, substitution of Asp with Ala ($\gamma^{1-17}_{D16A}$) results in a higher binding affinity. Absence of a strong interaction with Lys12 in the ClfA-peptide complex structure also correlates with the biochemical data, suggesting that Arg is not a key player in the ClfA-Fg interaction. In general, the present invention shows that K406 and D410, which are essential for platelet integrin $\alpha_{IIb}\beta_3$-Fg interaction, are dispensable for the ClfA-Fg interaction. Thus, although ClfA and $\alpha_{IIb}\beta_3$ target the same stretch of amino acids in Fg, there are significant differences in the binding interactions.

EXAMPLE 20

The $g^{1-17}_{D16A}$ and $g^{1-17}_{K12A}$ Peptides are Selective Antagonists of Fg-ClfA Interaction Although ClfA and $\alpha_{IIb}\beta_3$ target the same stretch of amino acids in Fg, there are significant differences in the binding interactions. Two of the series of peptides, $g^{1-17}_{D16A}$ and $g^{1-17}_{K12A}$, synthesized earlier for the characterization of WT $g^{1-17}$ peptide, lack Asp and Lys residues respectively at positions 416 and 410. These residues are quintessential for Fg binding to plate integrin $\alpha_{IIb}\beta_3$. The, $g^{1-17}_{D16A}$ and $g^{1-17}_{K12A}$ peptides either shows similar or enhanced binding to ClfA (FIGS. 1B, 1D) but are expected to bind weakly to platelet integrin. Therefore, $g^{1-17}_{D16A}$ and $g^{1-17}_{K12A}$ peptides could serve as selective antagonist of Fg-ClfA interaction.

Figure 6:
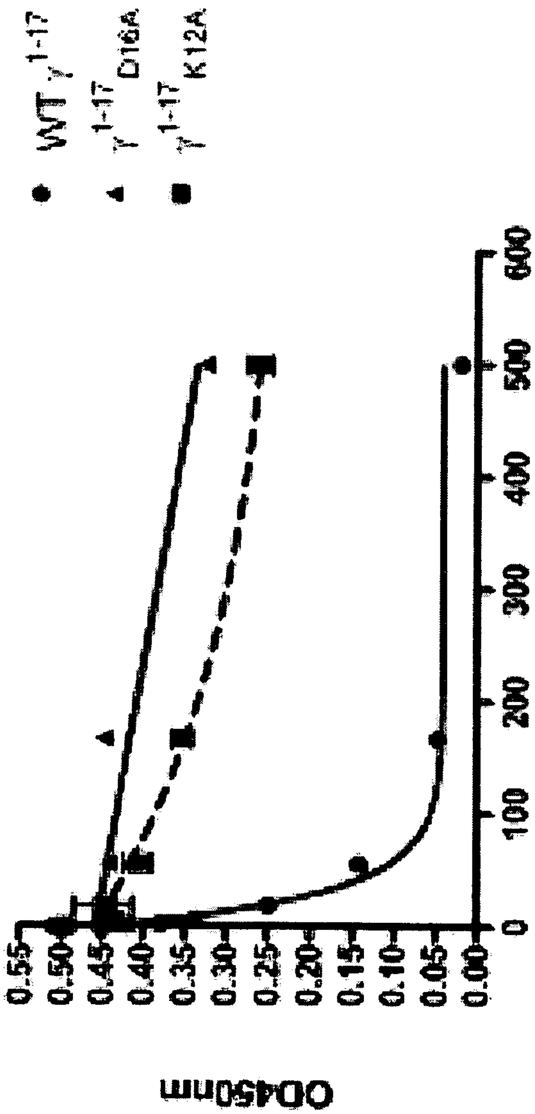
FIG. 6 illustrates that the $\gamma^{1-17}{}_{D16A}$ and $\gamma^{1-17}{}_{K12A}$ peptides bind weakly to platelet integrin $\alpha_{IIb}\beta_3$. Inhibition of Fg γ peptides ($\gamma^{1-17}{}_{D16A}$ and $\gamma^{1-17}{}_{K12A}$ and $\gamma^{1-17}$; WT) on binding of full length Fg immobilized onto $\alpha_{IIb}\beta_3$. Wild-type Fg-$\gamma^{1-17}$ peptide (square) inhibits Fg binding to $\alpha_{IIb}\beta_3$ whereas $\gamma^{1-17}{}_{D16A}$ (triangle) and $\gamma^{1-17}{}_{K12A}$ (inverted triangle) peptides have very little inhibitory effect.

To examine this possibility, the ability of the synthesized Fg WT $g^{1-17}$ and mutated peptides ($g^{1-17}_{D16A}$ and $g^{1-17}_{K12A}$) to inhibit full length Fg binding to $\alpha_{IIb}\beta_3$ was analyzed by inhibitory ELISA type assay (FIG. 6). The WT, $g^{1-17}$ peptide completely inhibited the binding of full-length fibrinogen to $\alpha_{IIb}\beta_3$ whereas, $g^{1-17}_{D16A}$ and $g^{1-17}_{K12A}$ weakly inhibited Fg binding $\alpha_{IIb}\beta_3$. These results clearly demonstrated that the $g^{1-17}_{D16A}$ and $g^{1-17}_{K12A}$ peptides bind weakly to platelet integrin and therefore could serve as an antagonist of Fg-ClfA interaction.

The following references were cited herein:

1. Lowy, F. D. (1998) N Engl J Med, 339:520-532.
2. Kristinsson, K. G. (1989) J Med Microbiol, 28:249-257.
3. Maltezou, H. C. and Giamarellou, H. (2006) Int J Antimicrob Agents, 27:87-96.
4. Weber (2005) Clin Infect Dis, 41 Suppl 4:S269-272.
5. Dinges et al (2000) Clin Microbiol Rev, 13:16-34.
6. Foster (2005) Nat Rev Microbiol, 3:948-958.
7. Foster and Höök, M. (1998) Trends Microbiol, 6:484-488.
8. O'Riordan, K. and Lee, J. C. (2004) Clin Microbiol Rev, 17:218-234.
9. McDevitt et al. (1997) Eur J Biochem, 247:416-424.
10. O'Brien et al. (2002) Mol Microbiol, 44:1033-1044.
11. Peacock et al. (2002) Infect Immun, 70:4987-4996.
12. Josefsson et al (2001) J Infect Dis, 184:1572-1580.
13. Que. et al (2001) Infect Immun, 69:6296-6302.
14. Siboo et al. (2001) Infect Immun, 69:3120-3127
15. Sullam et al (1996) Infect Immun, 64:4915-4921.
16. Hall et al. (2003) Infect Immun, 71:6864-6870.
17. Domanski et al. (2005) Infect Immun, 73:5229-5232.
18. Patti, J. M. (2004) Vaccine, 22 Suppl 1:S39-43.
19. Marraffini et al (2006) Microbiol Mol Biol Rev, 70:192-221.
20. Mazmanian et al. (2001) Mol Microbiol, 40:1049-1057.
21. McDevitt et al (1994) Mol Microbiol, 11:237-248.
22. Ni Eidhin et al. (1998) Mol Microbiol, 30:245-257.
23. Wann et al. (2000) J Biol Chem, 275:13863-13871.
24. Deivanayagam et al. (2002) Embo J, 21:6660-6672.
25. Ponnuraj et al. (2003) Cell, 115:217-228.
26. Farrell et al (1992) Proc Natl Acad Sci USA, 89:10729-10732.
27. Hettasch. et al (1992) Thromb Haemost, 68:701-706.
28. Kloczewiak et al (1989) Biochemistry, 28:2915-2919.
29. Zong et al. (2005) Embo J, 24:4224-4236.
30. Sambrook, J. and Gething, M. J. (1989) Nature, 342:224-225.
31. Hartford et al (2001) J Biol Chem, 276:2466-2473.
32. Bowden et al. (2008) J Biol Chem, 283:638-647.
33. Ho et al. (1989) Gene, 77:51-59.
34. Horton et al (1990) Biotechniques, 8:528-535.
35. O'Connell et al (1998) J Biol Chem, 273:6821-6829.
36. McCoy, A. J. et al. (2005) Acta Crystallogr D Biol Crystallogr, 61:458-464.
37. Emsley and Cowtan, (2004) Acta Crystallogr D Biol Crystallogr, 60:2126-2132.
38. Perrakis et al (2001) Acta Crystallogr D Biol Crystallogr, 57:1445-1450.
39. Murshudov et al (1997) Acta Crystallogr D Biol Crystallogr, 53:240-255.
40. Laskowski et al. (1993) J Mol Biol, 231:1049-1067.
41. Huang, X. and Miller, W. (1991) Adv. Appl. Math, 12:337-357.
42. Carson, M. J. (1997) J. Mol. Graph., 5:03-106.
43. Keane et al. (2007) Mol Microbiol, 63:711-723.
44. McDevitt et al (1995) Mol Microbiol, 16:895-907.
45. Xiao et al. (2004) Nature, 432:59-67.
46. Xiong et al. (2002) Science, 296:151-155.
47. Pflugrath, J. W. (1999) Acta Crystallogr D Biol Crystallogr, 55:1718-1725.

What is claimed is:

1. A method for determining the structure of a microbial surface components recognizing adhesive matrix molecule in complex with fibrinogen, comprising the steps of:

- providing a Clumping factor A ClfA complexed with a fibrinogen gamma-peptide;
- determining a ClfA binding region of the fibrinogen gamma-peptide;
- determining one or more critical amino acid residues in the ClfA binding region of a native fibrinogen gamma-peptide that is critical for a ClfA:fibrinogen gamma-peptide interaction;
- determining one or more amino acid residues of the ClfA that binds to the ClfA binding region of the native fibrinogen gamma-peptide;
- modeling the structure of the ClfA binding region;
- performing computational modeling of the ClfA sequence that binds to the ClfA binding region of native fibrinogen, thereby determining the structure of the ClfA:fibrinogen gamma-peptide interaction; and
- identifying one or more potential agents that inhibit the ClfA:fibrinogen gamma-peptide interaction without affecting binding of other proteins to the fibrinogen gamma-peptide.

2. The method of claim 1, further comprising identifying one or more potential agents with at least one different amino acid from the native fibrinogen that inhibit ClfA:fibrinogen gamma-peptide interaction without affecting binding of other proteins to fibrinogen gamma-peptide.

3. The method of claim 2, wherein the one or more potential agents comprise an amino acid sequence of the ClfA binding region on fibrinogen gamma-peptide that differs from the fibrinogen gamma-peptide by at least one amino acid and differs from the ClfA by at least one amino acid.

4. The method of claim 1, further comprising the steps of

- synthesizing one or more control peptides that comprise the native fibrinogen gamma-peptide sequence that binds the ClfA;
- synthesizing one or more substituted peptides that differ from the one or more control peptides by one or more amino acid residues; and
- comparing binding of the ClfA to native fibrinogen gamma-peptide in the presence of the one or more control peptides or in the presence of the one or more substituted peptides, wherein less potent inhibition of the ClfA binding to the native fibrinogen gamma-peptide in the presence of the substituted peptide compared to the one or more control peptides indicates that the amino acid residues that were substituted are less important for the ClfA:fibrinogen gamma-peptide interaction, and wherein extensive inhibition of the ClfA binding to native fibrinogen gamma-peptide in the presence of the one or more substituted peptides compared to the one or more control peptides indicates that the amino acid residue that were substituted are critical for the ClfA:fibrinogen gamma-peptide interaction to determine the one or more critical amino acid residues.

5. The method of claim 1, wherein the amino acid residue in the ClfA is determined by comparing the stability of a native ClfA:fibrinogen gamma-peptide complex with the stability of a mutated ClfA:fibrinogen gamma-peptide complex, wherein said fibrinogen gamma-peptide in the complex comprises a peptide derived from the ClfA binding region of native fibrinogen gamma-peptide.

6. The method of claim 1, wherein said ClfA is present on the surface of *Staphylococcus aureus, Staphylococcus lugdunensis*, or *Staphylococcus epidermidis.*

7. The method of claim 1, wherein the native fibrinogen comprises a K406A peptide, a D410A peptide, or a K406A and D410A peptide.

8. The method of claim 1, wherein the other proteins to the fibrinogen gamma-peptide comprises integrin $\alpha_{IIb}\beta_3$.

* * * * *

SEQUENCE LISTING

```
<160> NUMBER OF SEQ ID NOS: 31

<210> SEQ ID NO 1
<211> LENGTH: 27
<212> TYPE: DNA
<213> ORGANISM: artificial sequence
<220> FEATURE:
<223> OTHER INFORMATION: ClfA229 synthetic oligonucleotide to amplify
      ClfA 229-545 gene product

<400> SEQUENCE: 1

cccggatccg gcacagatat tacgaat                                         27


<210> SEQ ID NO 2
<211> LENGTH: 30
<212> TYPE: DNA
<213> ORGANISM: artificial sequence
<220> FEATURE:
<223> OTHER INFORMATION: ClfA545 synthetic oligonucleotide to amplify
```

ClfA 229-545 gene product

<400> SEQUENCE: 2
cccggtacct caaggaacaa ctggtttatc 30

<210> SEQ ID NO 3
<211> LENGTH: 27
<212> TYPE: DNA
<213> ORGANISM: artificial sequence
<220> FEATURE:
<223> OTHER INFORMATION: rClfA327 synthetic oligonucleotide to amplify
SdrG 273-597 disulfide mutant

<400> SEQUENCE: 3
tgcttttaca tcacatttag tatttac 27

<210> SEQ ID NO 4
<211> LENGTH: 27
<212> TYPE: DNA
<213> ORGANISM: artificial sequence
<220> FEATURE:
<223> OTHER INFORMATION: fClfA327 synthetic oligonucleotide to amplify
SdrG 273-597 disulfide mutant

<400> SEQUENCE: 4
gtaaatacta aatgtgatgt aaaagca 27

<210> SEQ ID NO 5
<211> LENGTH: 39
<212> TYPE: DNA
<213> ORGANISM: artificial sequence
<220> FEATURE:
<223> OTHER INFORMATION: ClfA545 synthetic oligonucleotide to amplify
ClfA 221-559 gene product

<400> SEQUENCE: 5
cccggtacct caaggaacaa ctggacaatc gataccgtc 39

<210> SEQ ID NO 6
<211> LENGTH: 17
<212> TYPE: PRT
<213> ORGANISM: artificial sequence
<220> FEATURE:
<223> OTHER INFORMATION: wild-type fibrinogen gamma chain 395-411
peptide

<400> SEQUENCE: 6

Gly Glu Gly Gln Gln His His Leu Gly Gly Ala Lys Gln Ala Gly
1 5 10 15

Asp Val

<210> SEQ ID NO 7
<211> LENGTH: 15
<212> TYPE: PRT
<213> ORGANISM: artificial sequence
<220> FEATURE:
<223> OTHER INFORMATION: mutant fibrinogen gamma3-17 D16A peptide

<400> SEQUENCE: 7

Gly Gln Gln His His Leu Gly Gly Ala Lys Gln Ala Gly Ala Val
1 5 10 15

<210> SEQ ID NO 8
<211> LENGTH: 12
<212> TYPE: PRT
<213> ORGANISM: artificial sequence
<220> FEATURE:

-continued

<223> OTHER INFORMATION: mutant fibrinogen gamma5-17 D16A peptide

<400> SEQUENCE: 8

His His Leu Gly Gly Ala Lys Gln Ala Gly Ala Val
1 5 10

<210> SEQ ID NO 9
<211> LENGTH: 11
<212> TYPE: PRT
<213> ORGANISM: artificial sequence
<220> FEATURE:
<223> OTHER INFORMATION: mutant fibrinogen gamma7-17 D16A peptide

<400> SEQUENCE: 9

His Leu Gly Gly Ala Lys Gln Ala Gly Ala Val
1 5 10

<210> SEQ ID NO 10
<211> LENGTH: 9
<212> TYPE: PRT
<213> ORGANISM: artificial sequence
<220> FEATURE:
<223> OTHER INFORMATION: mutant fibrinogen gamma9-17 D16A peptide

<400> SEQUENCE: 10

Gly Gly Ala Lys Gln Ala Gly Ala Val
1 5

<210> SEQ ID NO 11
<211> LENGTH: 15
<212> TYPE: PRT
<213> ORGANISM: artificial sequence
<220> FEATURE:
<223> OTHER INFORMATION: wildtype fibrinogen gamma1-15 peptide

<400> SEQUENCE: 11

Gly Glu Gly Gln Gln His His Leu Gly Gly Ala Lys Gln Ala Gly
1 5 10 15

<210> SEQ ID NO 12
<211> LENGTH: 13
<212> TYPE: PRT
<213> ORGANISM: artificial sequence
<220> FEATURE:
<223> OTHER INFORMATION: wildtype fibrinogen gamma1-13 peptide

<400> SEQUENCE: 12

Gly Glu Gly Gln Gln His His Leu Gly Gly Ala Lys Gln
1 5 10

<210> SEQ ID NO 13
<211> LENGTH: 17
<212> TYPE: PRT
<213> ORGANISM: artificial sequence
<220> FEATURE:
<223> OTHER INFORMATION: fibrinogen gamma 395-411 peptide with G1A mutation

<400> SEQUENCE: 13

Ala Glu Gly Gln Gln His His Leu Gly Gly Ala Lys Gln Ala Gly
1 5 10 15

Ala Val

<210> SEQ ID NO 14
<211> LENGTH: 17
<212> TYPE: PRT
<213> ORGANISM: artificial sequence -continued

```
<220> FEATURE:
<223> OTHER INFORMATION: fibrinogen gamma 395-411 peptide with E2A
      mutation

<400> SEQUENCE: 14

Gly Ala Gly Gln Gln His His Leu Gly Gly Ala Lys Gln Ala Gly
1               5                   10                  15

Ala Val


<210> SEQ ID NO 15
<211> LENGTH: 17
<212> TYPE: PRT
<213> ORGANISM: artificial sequence
<220> FEATURE:
<223> OTHER INFORMATION: fibrinogen gamma 395-411 peptide with G3A
      mutation

<400> SEQUENCE: 15

Gly Glu Ala Gln Gln His His Leu Gly Gly Ala Lys Gln Ala Gly
1               5                   10                  15

Ala Val


<210> SEQ ID NO 16
<211> LENGTH: 17
<212> TYPE: PRT
<213> ORGANISM: artificial sequence
<220> FEATURE:
<223> OTHER INFORMATION: fibrinogen gamma 395-411 peptide with Q4A
      mutation

<400> SEQUENCE: 16

Gly Glu Gly Ala Gln His His Leu Gly Gly Ala Lys Gln Ala Gly
1               5                   10                  15

Ala Val


<210> SEQ ID NO 17
<211> LENGTH: 17
<212> TYPE: PRT
<213> ORGANISM: artificial sequence
<220> FEATURE:
<223> OTHER INFORMATION: fibrinogen gamma 395-411 peptide with Q5A
      mutation

<400> SEQUENCE: 17

Gly Glu Gly Gln Ala His His Leu Gly Gly Ala Lys Gln Ala Gly
1               5                   10                  15

Ala Val


<210> SEQ ID NO 18
<211> LENGTH: 17
<212> TYPE: PRT
<213> ORGANISM: artificial sequence
<220> FEATURE:
<223> OTHER INFORMATION: fibrinogen gamma 395-411 peptide with H6A
      mutation

<400> SEQUENCE: 18

Gly Glu Gly Gln Gln Ala His Leu Gly Gly Ala Lys Gln Ala Gly
1               5                   10                  15

Ala Val


<210> SEQ ID NO 19
<211> LENGTH: 17
<212> TYPE: PRT
<213> ORGANISM: artificial sequence
```

<220> FEATURE:
<223> OTHER INFORMATION: fibrinogen gamma 395-411 peptide with H7A mutation

<400> SEQUENCE: 19

Gly Glu Gly Gln Gln His Ala Leu Gly Gly Ala Lys Gln Ala Gly
1 5 10 15

Ala Val

<210> SEQ ID NO 20
<211> LENGTH: 17
<212> TYPE: PRT
<213> ORGANISM: artificial sequence
<220> FEATURE:
<223> OTHER INFORMATION: fibrinogen gamma 395-411 peptide with L8A mutation

<400> SEQUENCE: 20

Gly Glu Gly Gln Gln His His Ala Gly Gly Ala Lys Gln Ala Gly
1 5 10 15

Ala Val

<210> SEQ ID NO 21
<211> LENGTH: 17
<212> TYPE: PRT
<213> ORGANISM: artificial sequence
<220> FEATURE:
<223> OTHER INFORMATION: fibrinogen gamma 395-411 peptide with G9A mutation

<400> SEQUENCE: 21

Gly Glu Gly Gln Gln His His Leu Ala Gly Ala Lys Gln Ala Gly
1 5 10 15

Ala Val

<210> SEQ ID NO 22
<211> LENGTH: 17
<212> TYPE: PRT
<213> ORGANISM: artificial sequence
<220> FEATURE:
<223> OTHER INFORMATION: fibrinogen gamma 395-411 peptide with G10A mutation

<400> SEQUENCE: 22

Gly Glu Gly Gln Gln His His Leu Gly Ala Ala Lys Gln Ala Gly
1 5 10 15

Ala Val

<210> SEQ ID NO 23
<211> LENGTH: 17
<212> TYPE: PRT
<213> ORGANISM: artificial sequence
<220> FEATURE:
<223> OTHER INFORMATION: fibrinogen gamma 395-411 peptide with A11S mutation

<400> SEQUENCE: 23

Gly Glu Gly Gln Gln His His Leu Gly Gly Ser Lys Gln Ala Gly
1 5 10 15

Ala Val

<210> SEQ ID NO 24
<211> LENGTH: 17
<212> TYPE: PRT
<213> ORGANISM: artificial sequence
<220> FEATURE:
<223> OTHER INFORMATION: fibrinogen gamma 395-411 peptide with K12A
mutation

<400> SEQUENCE: 24

Gly Glu Gly Gln Gln His His Leu Gly Gly Ala Ala Gln Ala Gly
1 5 10 15

Ala Val

<210> SEQ ID NO 25
<211> LENGTH: 17
<212> TYPE: PRT
<213> ORGANISM: artificial sequence
<220> FEATURE:
<223> OTHER INFORMATION: fibrinogen gamma 395-411 peptide with Q13A
mutation

<400> SEQUENCE: 25

Gly Glu Gly Gln Gln His His Leu Gly Gly Ala Lys Ala Ala Gly
1 5 10 15

Ala Val

<210> SEQ ID NO 26
<211> LENGTH: 17
<212> TYPE: PRT
<213> ORGANISM: artificial sequence
<220> FEATURE:
<223> OTHER INFORMATION: fibrinogen gamma 395-411 peptide with A14S
mutation

<400> SEQUENCE: 26

Gly Glu Gly Gln Gln His His Leu Gly Gly Ala Lys Gln Ser Gly
1 5 10 15

Ala Val

<210> SEQ ID NO 27
<211> LENGTH: 17
<212> TYPE: PRT
<213> ORGANISM: artificial sequence
<220> FEATURE:
<223> OTHER INFORMATION: fibrinogen gamma 395-411 peptide with G15A
mutation

<400> SEQUENCE: 27

Gly Glu Gly Gln Gln His His Leu Gly Gly Ala Lys Gln Ala Ala
1 5 10 15

Ala Val

<210> SEQ ID NO 28
<211> LENGTH: 17
<212> TYPE: PRT
<213> ORGANISM: artificial sequence
<220> FEATURE:
<223> OTHER INFORMATION: fibrinogen gamma 395-411 peptide with D16A
mutation

<400> SEQUENCE: 28

Gly Glu Gly Gln Gln His His Leu Gly Gly Ala Lys Gln Ala Gly
1 5 10 15

Ala Val

<210> SEQ ID NO 29
<211> LENGTH: 17
<212> TYPE: PRT
<213> ORGANISM: artificial sequence -continued

```
<220> FEATURE:
<223> OTHER INFORMATION: fibrinogen gamma 395-411 peptide with V17A
      mutation

<400> SEQUENCE: 29

Gly Glu Gly Gln Gln His His Leu Gly Gly Ala Lys Gln Ala Gly
1               5                   10                  15

Ala Ala


<210> SEQ ID NO 30
<211> LENGTH: 6
<212> TYPE: PRT
<213> ORGANISM: artificial sequence
<220> FEATURE:
<223> OTHER INFORMATION: ligand sequence recognized by platelet
      specific integrin ?IIb?3

<400> SEQUENCE: 30

Lys Gln Ala Gly Asp Val
1               5


<210> SEQ ID NO 31
<211> LENGTH: 17
<212> TYPE: PRT
<213> ORGANISM: artificial sequence
<220> FEATURE:
<223> OTHER INFORMATION: bovine fibrinogen gamma chain peptide
      homologous to wildtype human fibrinogen gamma chain peptide
      395-411

<400> SEQUENCE: 31

Gly Glu Gly Gln Gln His His Leu Gly Gly Ala Lys Gln Val Gly
1               5                   10                  15

Val Glu
```